(12) United States Patent
Overes

(10) Patent No.: US 9,999,453 B2
(45) Date of Patent: Jun. 19, 2018

(54) FEMORAL NECK FRACTURE IMPLANT

(71) Applicant: DePuy Synthes Products, Inc., Raynham, MA (US)

(72) Inventor: Tom Overes, Oberdorf (CN)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 0 days. days.

(21) Appl. No.: 15/494,735

(22) Filed: Apr. 24, 2017

(65) Prior Publication Data

US 2017/0224395 A1    Aug. 10, 2017

Related U.S. Application Data

(63) Continuation of application No. 13/676,832, filed on Nov. 14, 2012, now Pat. No. 9,662,156.

(60) Provisional application No. 61/561,439, filed on Nov. 18, 2011, provisional application No. 61/692,053, filed on Aug. 22, 2012.

(51) Int. Cl.
| | |
|---|---|
| *A61B 17/88* | (2006.01) |
| *A61B 17/74* | (2006.01) |
| *A61B 17/86* | (2006.01) |
| *A61B 17/80* | (2006.01) |
| *A61B 17/90* | (2006.01) |

(52) U.S. Cl.
CPC ........ *A61B 17/746* (2013.01); *A61B 17/8057* (2013.01); *A61B 17/863* (2013.01); *A61B 17/8605* (2013.01); *A61B 2017/90* (2013.01)

(58) Field of Classification Search
CPC .............. A61B 17/7208; A61B 17/725; A61B 17/7258; A61B 17/68; A61B 17/863; A61B 2019/5466

USPC ....................................... 606/62–67, 280–299
See application file for complete search history.

(56) References Cited

U.S. PATENT DOCUMENTS

| | | | |
|---|---|---|---|
| 2,526,959 | A | 10/1950 | Lorenzo |
| 3,216,414 | A | 11/1965 | Street |
| 3,374,786 | A | 3/1968 | Callender |
| 3,530,854 | A | 9/1970 | Kearney |
| 3,554,193 | A | 1/1971 | Konstantinou et al. |
| 4,172,452 | A | 10/1979 | Forte et al. |

(Continued)

FOREIGN PATENT DOCUMENTS

| | | |
|---|---|---|
| CN | 2384587 | 6/2000 |
| CN | 1269198 | 10/2000 |

(Continued)

*Primary Examiner* — Corrine McDermott
*Assistant Examiner* — Tara R Carter
(74) *Attorney, Agent, or Firm* — Fay Kaplun & Marcin, LLP

(57) ABSTRACT

A bone fixation system comprises an elongated implant shaft extending from a proximal end to a distal end along a central longitudinal axis and including a first channel extending from the proximal end to a side opening formed in a side wall of the implant shaft along a first channel axis. The bone fixation system further comprises a bone plate having a first plate portion and a second plate portion, the first plate portion having a first opening extending therethrough along a first opening axis and the second plate portion having a second opening extending therethrough along a second opening axis, the second opening being configured to receive the implant shaft therethrough to permit insertion thereof into a head of a bone.

19 Claims, 33 Drawing Sheets

(56) References Cited

U.S. PATENT DOCUMENTS

| | | |
|---|---|---|
| 4,465,065 A | 8/1984 | Gotfried |
| 4,494,535 A | 1/1985 | Haig |
| 4,657,001 A | 4/1987 | Fixel |
| 4,791,918 A | 12/1988 | Von Hasselbach |
| 4,911,153 A | 3/1990 | Border |
| 5,116,336 A | 5/1992 | Frigg |
| 5,127,914 A | 7/1992 | Calderale et al. |
| 5,364,398 A | 11/1994 | Chapman et al. |
| 5,409,489 A | 4/1995 | Sioufi |
| 5,429,641 A | 7/1995 | Gotfried |
| 5,591,168 A | 1/1997 | Judet et al. |
| 5,658,339 A | 8/1997 | Tronzo et al. |
| 5,810,821 A | 9/1998 | Vandewalle |
| 6,206,885 B1 | 3/2001 | Ghahremani et al. |
| 6,409,768 B1 | 6/2002 | Tepic et al. |
| 7,001,388 B2 | 2/2006 | Orbay et al. |
| 7,118,572 B2 | 10/2006 | Bramlet et al. |
| 7,175,633 B2 | 2/2007 | Roth et al. |
| 7,527,627 B2 | 5/2009 | Ferrante et al. |
| 7,534,244 B2 | 5/2009 | Ferrante et al. |
| 7,670,341 B2 | 3/2010 | Leyden et al. |
| 7,918,853 B2 | 4/2011 | Watanabe et al. |
| 7,931,652 B2 | 4/2011 | Ferrante et al. |
| 8,182,484 B2 | 5/2012 | Grant et al. |
| 8,187,275 B2 | 5/2012 | Ferrante et al. |
| 8,328,806 B2 | 12/2012 | Tyber et al. |
| 8,398,636 B2 | 3/2013 | Simon et al. |
| 8,617,161 B2 | 12/2013 | Ferrante et al. |
| 2003/0083667 A1 | 5/2003 | Ralph et al. |
| 2004/0193162 A1 | 9/2004 | Bramlet et al. |
| 2005/0055024 A1 | 3/2005 | James et al. |
| 2005/0085818 A1 | 4/2005 | Huebner |
| 2005/0192578 A1 | 9/2005 | Horst |
| 2006/0004361 A1* | 1/2006 | Hayeck ............... A61B 17/74 606/282 |
| 2006/0095044 A1 | 5/2006 | Grady, Jr. et al. |
| 2006/0106386 A1 | 5/2006 | Reber et al. |
| 2006/0189991 A1 | 8/2006 | Bickley |
| 2006/0241606 A1* | 10/2006 | Vachtenberg ...... A61B 17/1728 606/65 |
| 2007/0083213 A1 | 4/2007 | Siravo et al. |
| 2007/0219562 A1 | 9/2007 | Slone et al. |
| 2007/0270845 A1 | 11/2007 | Watanabe et al. |
| 2007/0270848 A1* | 11/2007 | Lin ..................... A61B 17/746 606/65 |
| 2008/0140130 A1 | 6/2008 | Chan et al. |
| 2008/0269807 A1 | 10/2008 | Simon et al. |
| 2008/0281326 A1 | 11/2008 | Watanabe et al. |
| 2009/0264885 A1 | 10/2009 | Grant et al. |
| 2010/0145397 A1 | 6/2010 | Overes et al. |
| 2010/0217265 A1 | 8/2010 | Chen et al. |
| 2010/0249852 A1 | 9/2010 | Brumbieled et al. |
| 2010/0256638 A1* | 10/2010 | Tyber ................. A61B 17/1717 606/62 |
| 2011/0066152 A1 | 3/2011 | Keller et al. |
| 2011/0087228 A1 | 4/2011 | Ferrante et al. |
| 2011/0106086 A1 | 5/2011 | Laird |
| 2011/0118739 A1 | 5/2011 | Tyber et al. |
| 2011/0230884 A1 | 9/2011 | Mantzaris et al. |
| 2011/0282398 A1 | 11/2011 | Overes et al. |
| 2013/0116694 A1 | 5/2013 | Zurschmiede |
| 2013/0296943 A1 | 11/2013 | Grady, Jr. et al. |
| 2014/0052132 A1 | 2/2014 | Matityahu |

FOREIGN PATENT DOCUMENTS

| | | |
|---|---|---|
| CN | 101304695 | 11/2008 |
| CN | 100542493 | 9/2009 |
| CN | 101778604 | 7/2010 |
| CN | 102715945 | 10/2012 |
| CN | 202665682 | 1/2013 |
| CN | 202960731 | 6/2013 |
| DE | 935859 | 12/1955 |
| EP | 0180532 | 5/1986 |
| EP | 1273271 | 1/2003 |
| EP | 2133034 | 12/2009 |
| JP | 8-112290 | 5/1996 |
| JP | 8-126650 | 5/1996 |
| JP | 2001/224600 | 8/2001 |
| JP | 2001/252283 | 9/2001 |
| JP | 2006/513766 | 4/2006 |
| JP | 2007-260446 | 10/2007 |
| JP | 2009/112594 | 5/2009 |
| JP | 2009/530035 | 8/2009 |
| JP | 2011-036716 | 2/2011 |
| WO | 2005/082263 | 9/2005 |
| WO | 2007/005614 | 1/2007 |
| WO | 2007/109302 | 9/2007 |
| WO | 2008/022136 | 2/2008 |
| WO | 2008/064211 | 5/2008 |
| WO | 2009/121144 | 10/2009 |
| WO | 2009/140742 | 11/2009 |
| WO | 2010/027891 | 3/2010 |
| WO | 2010/103494 | 9/2010 |
| WO | 2011/010974 | 1/2011 |
| WO | 2011/075757 | 6/2011 |
| WO | 2014/032522 | 3/2014 |

* cited by examiner

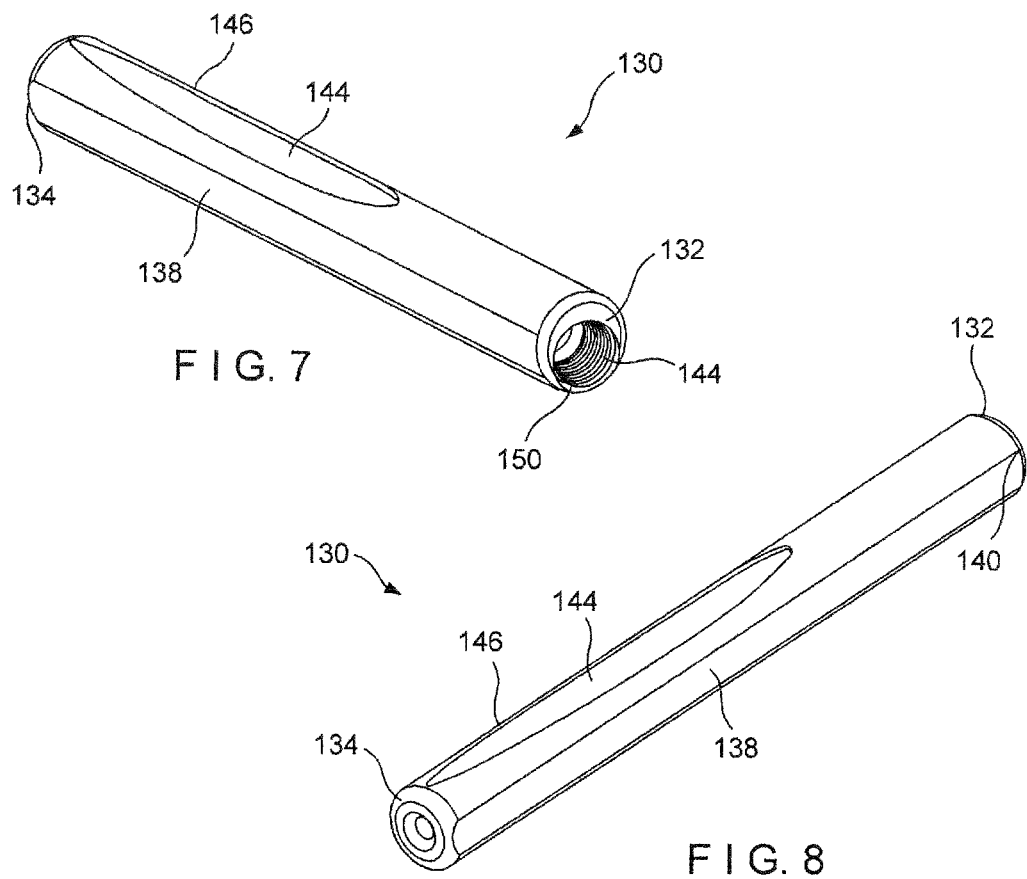
FIG. 7
FIG. 8
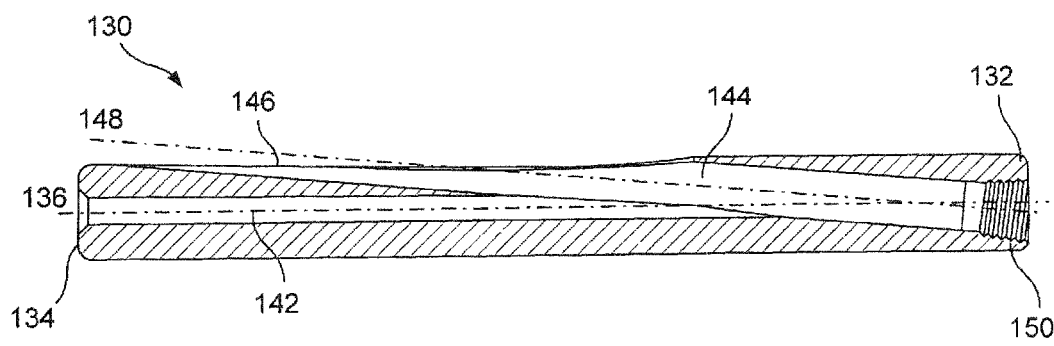
FIG. 9

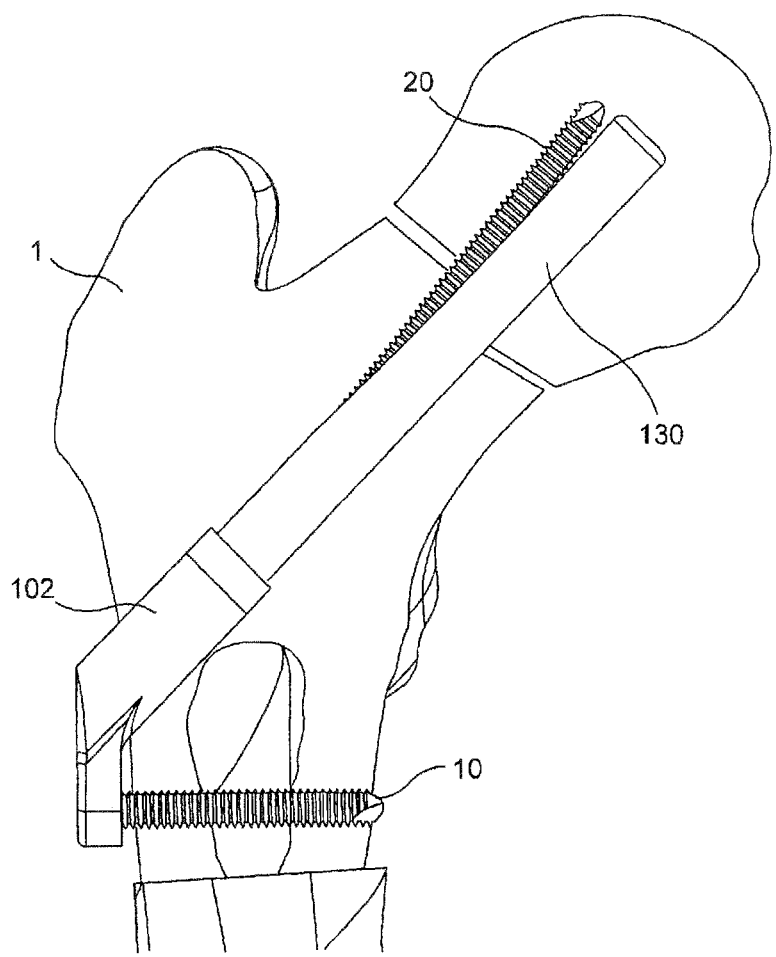
F I G. 20

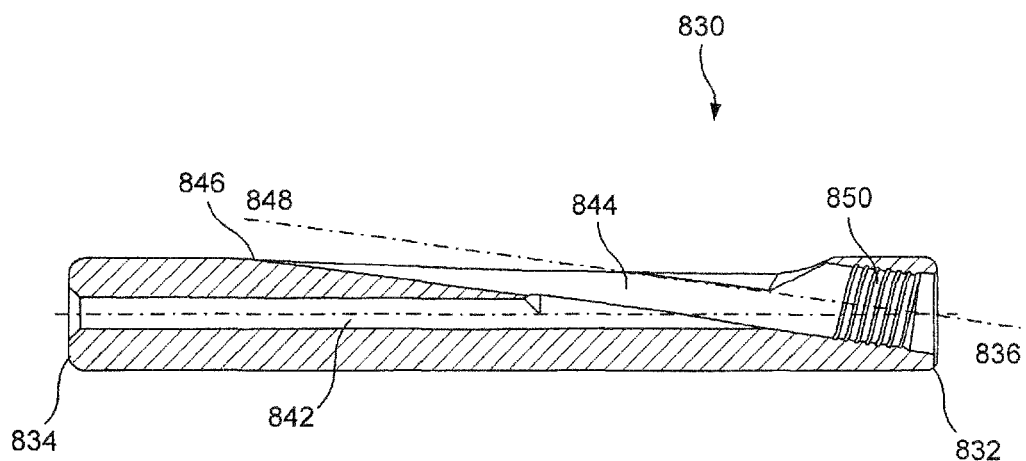
F I G. 43
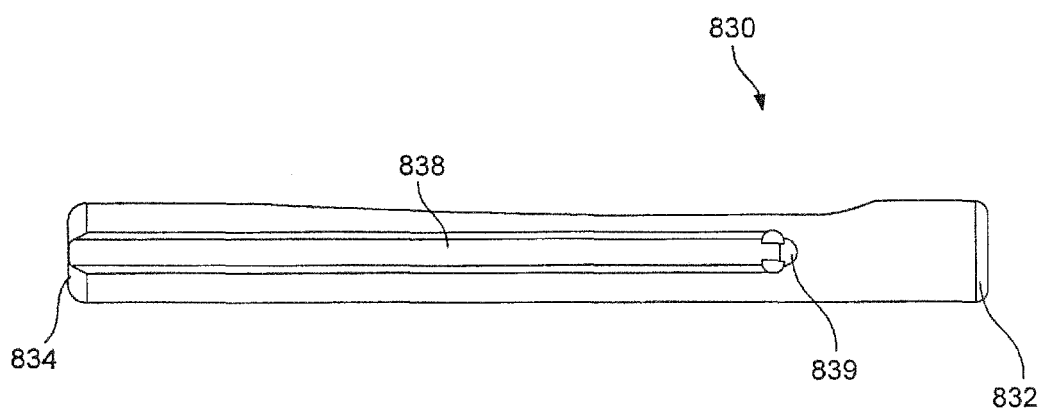
F I G. 44

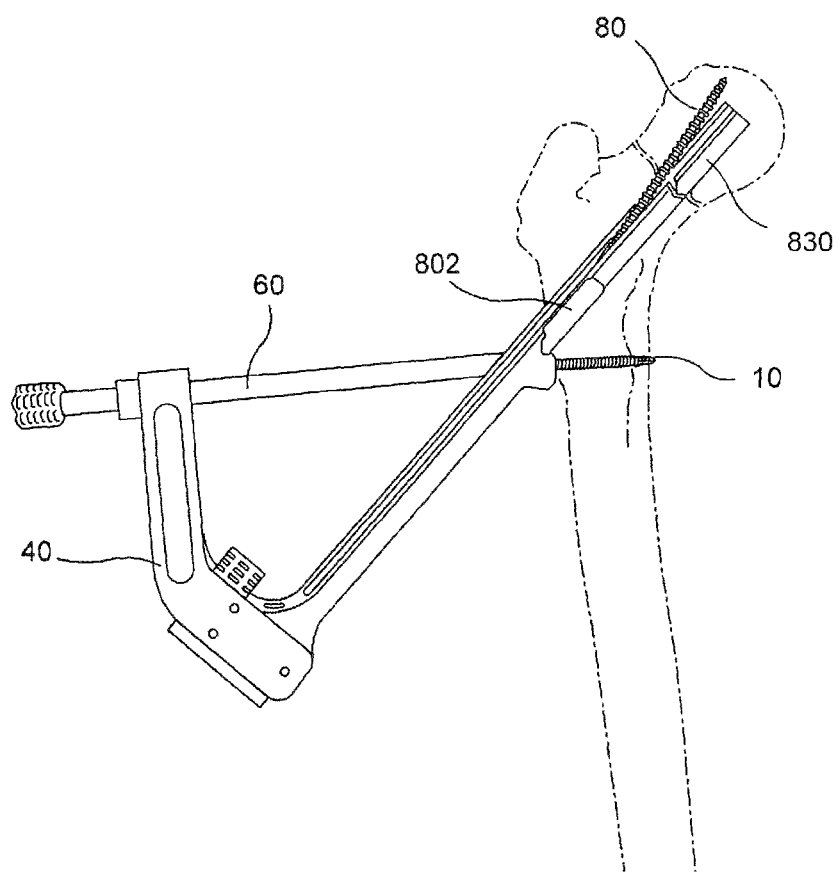
F I G. 50

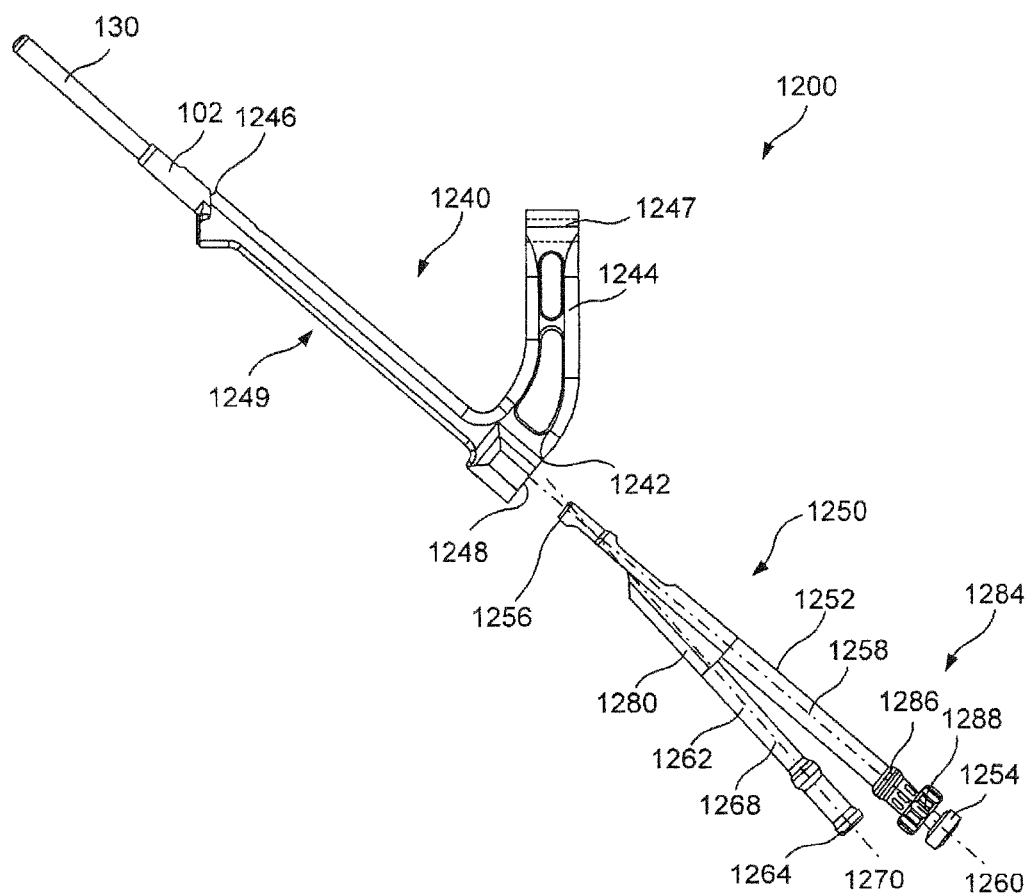
F I G. 57

FEMORAL NECK FRACTURE IMPLANT

PRIORITY CLAIM

The present application is a Continuation Application of U.S. patent application Ser. No. 13/676,832 filed on Nov. 14, 2012; which claims the priority to U.S. Provisional Application Ser. No. 61/561,439 filed on Nov. 18, 2011, and 61/692,053 filed on Aug. 22, 2012. The entire disclosures of these patents/applications are expressly incorporated herein by reference.

FIELD OF THE INVENTION

The present invention generally relates to fasteners, fastener assemblies, kits for fastener assemblies, methods of assembling fastener assemblies, and methods of implanting fastener assemblies in a bone.

BACKGROUND

Femoral neck fractures are often treated with a pin or other implant inserted into the femoral head along an axis of the femoral neck. One such product is the Stryker® Hansson® Pin System, which is a rod first and second ends separated from one another by a side wall with no threading on its outer surface. The Hansson® Pin has a hook deployable from a first end region for fixing the Hansson® Pin in the femoral head. The hook is deployed by pushing a shaft in the second end, which in turns deploys the hook through a hole in the side wall. Generally, two or three Hansson® pins are inserted into the femoral head to fix the femoral head and to facilitate healing of the femoral neck fracture.

Other known products for treatment of femoral neck fractures include the Stryker® Gamma3® Hip Fracture system and the Smith+Nephew® Trigen® Intertan® Trochanteric Nail system. Both these systems include an intramedullary nail insertable into the femur and have rod-like fasteners insertable through the intramedullary nail into the femoral head for stabilizing the femoral neck fracture. Additionally, each of these systems includes a feature for minimizing unwanted rotation of the femoral head relative to the rod-like fastener, which is fixed in the nail. After the fastener is fixed, medial migration of the femoral head relative to the neck fracture may cause an end of the rod-like fastener to perforate the femoral head and damage the hip-joint. Another known product is the Synthes® DHS® which includes a bone plate fixable to the femur in the vicinity of the femoral head. The bone plate is prevented from rotating once positioned by a plurality of bone screws extending through the plate into the femur. The bone plate includes a channel extending across a portion positioned to permit a rod-like fastener to be passed through the channel into the femoral head to stabilize the femoral head and allow healing of a femoral neck fracture. The rod-like fastener is impacted to drive it into the femoral head.

It is an object of the present invention to provide an improved system for femoral neck fracture fixation.

SUMMARY OF THE INVENTION

The present invention is directed to a bone fixation system, comprising an elongated implant shaft extending from a proximal end to a distal end along a central longitudinal axis and including a first channel extending from the proximal end to the distal end along a first channel axis and a second channel extending from the proximal end to a side opening formed in a side wall of the implant shaft along a second channel axis. The bone fixation system also comprises a bone plate having a first plate portion and a second plate portion, the first plate portion having a first opening extending therethrough along a first opening axis and the second plate portion having a second opening extending therethrough along a second opening axis, the second opening being configured to receive the implant shaft therethrough to permit insertion thereof into a head of a bone.

In a first aspect, the present invention provides a bone fixation element for supporting the healing of femoral neck fractures. The bone fastener according to the invention has an elongate implant shaft extending from a proximal end to a distal end with a first central longitudinal channel extending therethrough. The implant shaft according to the invention further includes a second channel extending from the first end to an opening in a side wall thereof. The first channel is configured to receive a guide wire therethrough while the second channel is configured to receive an anti-rotation member (e.g., a bone screw) therethrough. The second channel is arranged to support a leading end region of an anti-rotation member in a protruding position and to prevent the femoral head from rotating relative thereto.

The opening may have a multi-faceted surface arranged to releasably hold an anti-rotation member in position by threadedly coupling a proximal end thereof. The multi-faceted surface may, for example, be a thread.

An outer wall of the implant shaft is configured to prevent rotation thereof relative to a bone plate through which it is inserted. For example, the outer wall may include at least one flat surface arranged to mate with a corresponding flat surface of the bone plate. The position of the flat surface determines the orientation of the implant shaft when positioned through the bone plate. In one embodiment, two flat surfaces may be provided on opposing side walls of the implant shaft. It is noted, however, that any other configuration may be used without deviating from the scope of the invention. For example, the implant shaft may comprise only one flat extending along an outer wall thereof.

A distal portion of the outer wall of the implant shaft defines a bone engaging feature in a distal region thereof. The bone engaging feature may be one of a smooth surface, a screw thread or a fluted surface.

In a second aspect, the present invention provides a fastener assembly for use, for example, in the healing of femoral neck fractures. The fastener assembly has an implant shaft with proximal end distal ends spaced apart by a side wall and first and second channels extending therethrough. The first channel extends from the proximal end to the distal end. The second channel extends from the proximal end to a second end on a side wall of the implant shaft. The fastener assembly includes an anti-rotation member shaped and dimensioned to be positionable in the second channel. The anti-rotation member may, for example, be substantially rod-like with a leading end and a trailing end. The proximal end may be configured to hold the trailing end when the anti-rotation member is positioned therein. The second channel is shaped to support the anti-rotation member in a position in which it protrudes from the side wall into the femoral head to prevent rotation of the femoral head relative to the implant shaft. The anti rotation member may be formed as a bone screw with a threaded shaft.

In a third aspect, the present invention includes a kit for anti-rotatably fastening a first part to a second part. The kit may comprise one or more of a fastener according to the first aspect and/or a fastener assembly according to the second aspect along with instructions for deploying the fastener or assembly as described above to treat a femoral neck fracture.

In a fourth aspect, the present invention includes a method of implanting a bone fixation assembly into a bone, comprising: inserting an implant shaft through a second opening extending through a bone plate, the bone plate having a first plate portion and a second plate portion, the first plate portion having a first opening extending therethrough along a first opening axis and the second plate portion having the second opening extending therethrough along a second opening axis, the implant shaft extending from a proximal end to a distal end along a central longitudinal axis and including a first channel extending from the proximal end to the distal end along a first channel axis and a second channel extending from the proximal end to a side opening formed in a side wall thereof along a second channel axis; inserting the implant shaft into a shaft of the bone until the first portion of the bone plate is positioned over an outer surface of the bone and a portion of the second portion is received within a head of the bone; and inserting an anti-rotation screw through the second channel until a head of the screw locking engages the proximal end of the second channel and a distal end of a shaft of the screw extends out of the side opening into the bone to prevent rotation of a head of the bone relative to the implant shaft.

In a fifth aspect, the present invention includes a method of assembling a bone fixation assembly, comprising: inserting an implant shaft through a second opening extending through a bone plate, the implant shaft engaging the second opening with a form fit permitting gliding/telescoping thereof, the bone plate having a first plate portion and a second plate portion, the first plate portion having a first opening extending therethrough along a first opening axis and the second plate portion having the second opening extending therethrough along a second opening axis, the implant shaft extending from a proximal end to a distal end along a central longitudinal axis and including a first channel extending from the proximal end to the distal end along a first channel axis and a second channel extending from the proximal end to a side opening formed in a side wall thereof along a second channel axis.

BRIEF DESCRIPTION OF THE DRAWINGS

Several embodiments of the invention will be described in the following by way of example and with reference to the accompanying drawings in which:

FIG. 7 shows a first perspective view of an implant shaft of the bone fastener assembly of FIG. 1;

FIG. 8 shows a second perspective view of the implant shaft of FIG. 7;

FIG. 9 shows a cross-sectional view of the implant shaft of FIG. 7;

FIG. 20 shows a tenth surgical step for use of the bone fastener assembly of FIG. 1;

FIG. 43 shows a cross-sectional view of the implant shaft of FIG. 40;

FIG. 44 shows a side view of the implant shaft of FIG. 40;

FIG. 50 shows a fifth surgical step for use of the bone fastener assembly of FIG. 36;

FIG. 57 shows a perspective view of an insertion device for the implant according to the invention in a first operative configuration;

DETAILED DESCRIPTION

Figure 1:
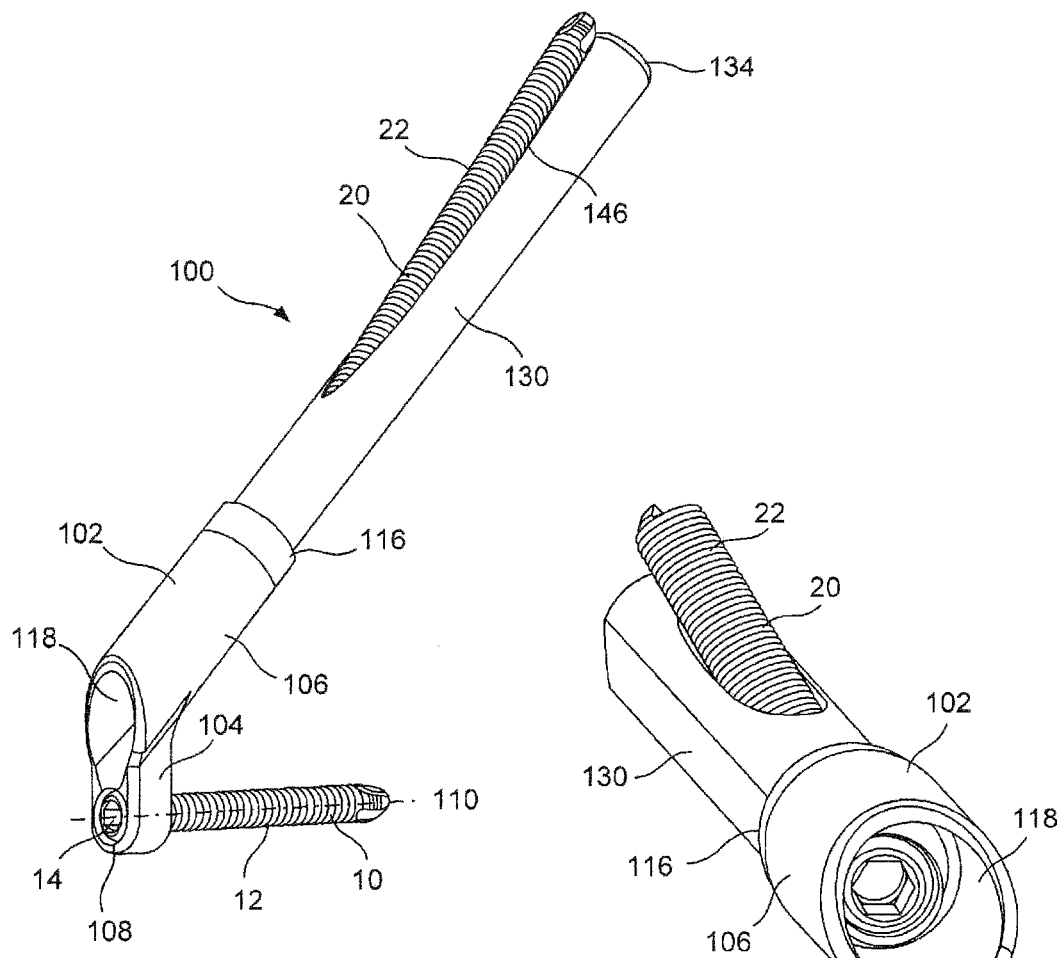
FIG. 1 shows a first perspective view of a bone fastener assembly according to a first exemplary embodiment of the invention.
Figure 2:
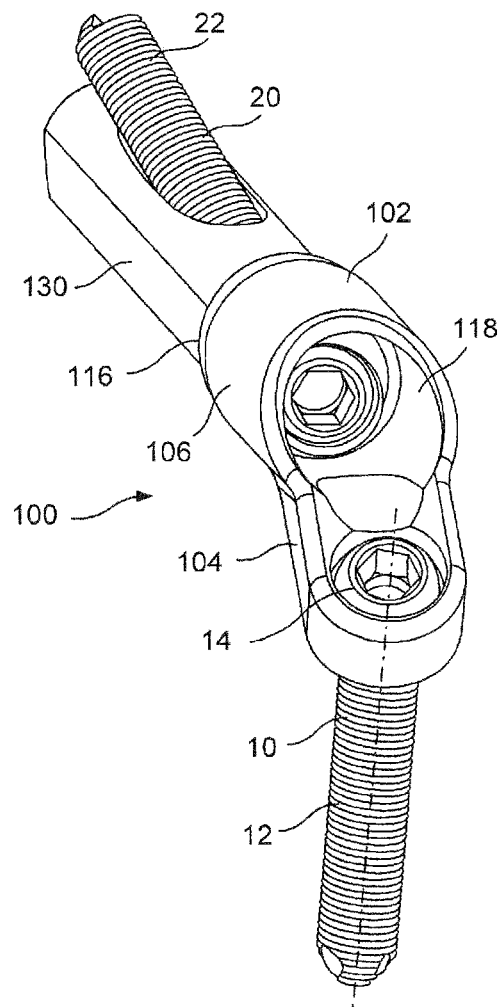
FIG. 2 shows a second perspective view of the bone fastener assembly of FIG. 1.
Figure 3:
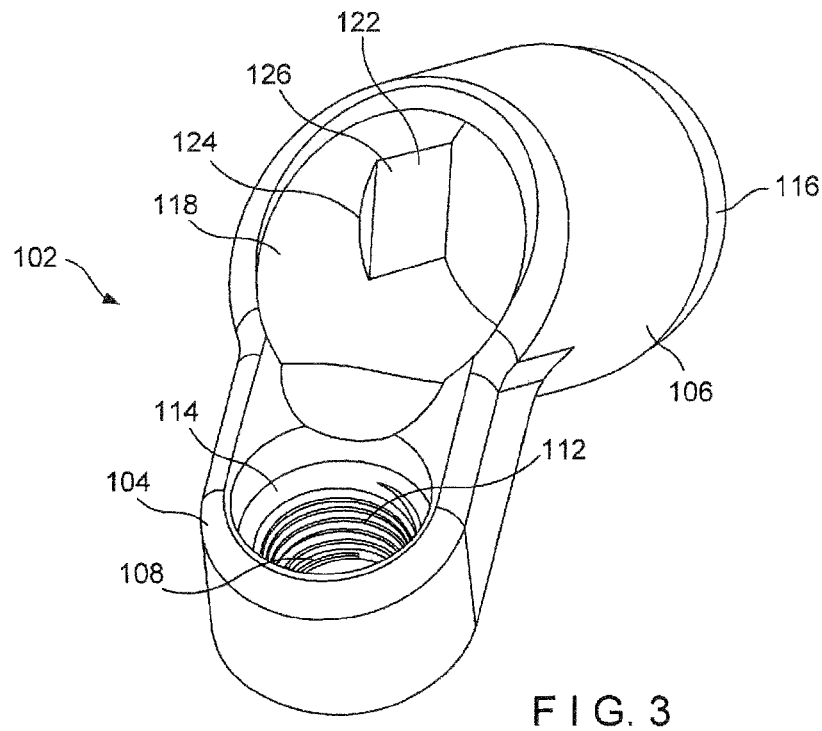
FIG. 3 shows a first perspective view of a bone plate of the bone fastener assembly of FIG. 1.
Figure 4:
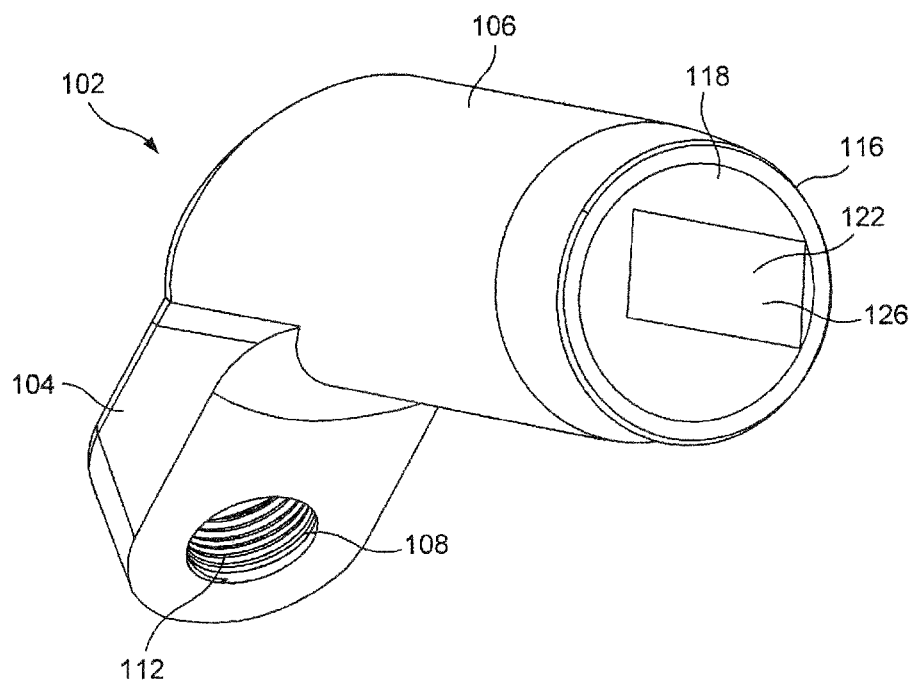
FIG. 4 shows a second perspective view of the bone plate of FIG. 3.
Figure 5:
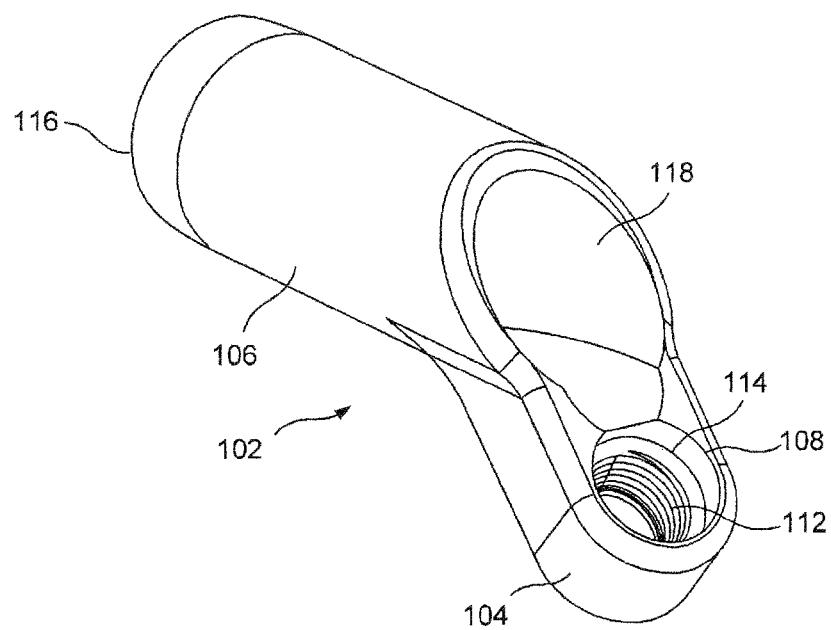
FIG. 5 shows a third perspective view of the bone plate of FIG. 3.
Figure 6:
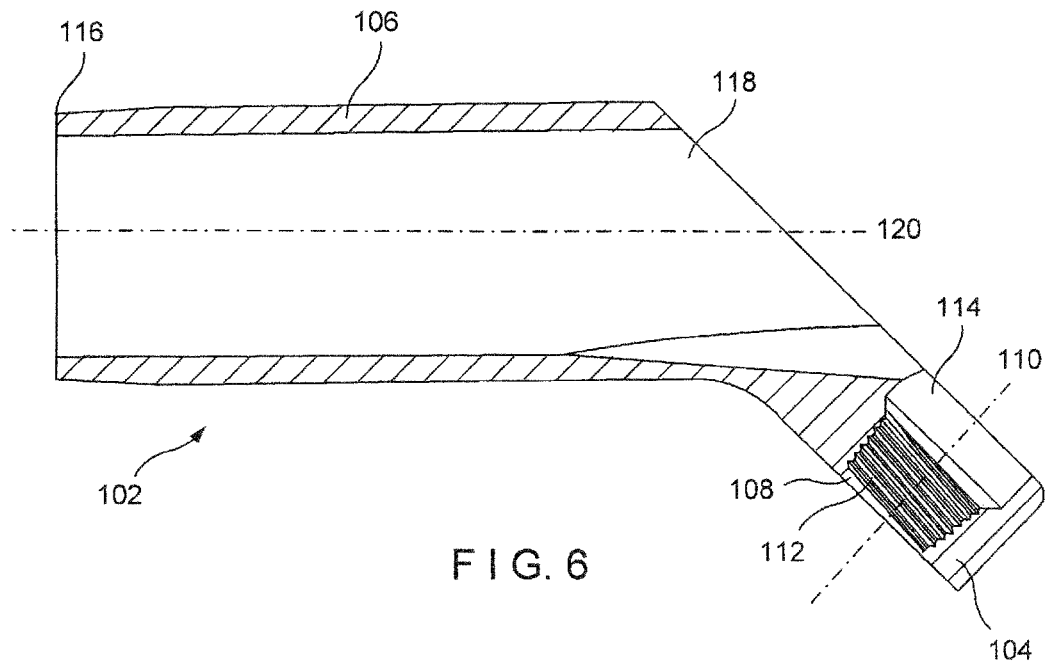
FIG. 6 shows a cross-sectional view of the bone plate of FIG. 3.

The present invention may be further understood with reference to the following description and the appended drawings, wherein like elements are referred to with the same reference numerals. The present invention relates to the treatment of fractures and, in particular, to devices for fixing femoral neck fractures. Exemplary embodiments of the present invention describe a bone plate having first portion positionable against an outer surface of a fractured or otherwise damaged bone and a second portion partially inserted into the bone. A first bone screw hole extends through the first portion and a second bone screw hole extends through the second portion. The second portion further receives a bone fixation shaft sized and dimensioned to extend across a fractured portion of the femoral neck into the femoral head. The bone fixation shaft includes a transverse opening extending through a side wall thereof along a transverse opening axis angled with respect to a bone fixation shaft axis such that a bone fixation element (e.g., a bone screw) inserted through the transverse opening extends away from the shaft into the bone to aid in fixation and compression of the fracture while also preventing rotation of the femoral head relative to the bone, as will be described in greater detail later on. It should be noted that the terms "proximal" and "distal" as used herein, refer to a direction toward (proximal) and away from (distal) a user of the device. In an exemplary embodiment, the system and method disclosed herein may be used for femoral neck fractures. It is noted that although the exemplary system and method are directed to a fixation of a femoral head fracture, the exemplary bone fixation system may be used in any other bone in the body without deviating from the scope of the invention.

The exemplary system and method according to the invention provide a minimally invasive surgical technique for treating femoral neck fractures using one or two incisions depending on soft-tissue thickness, as those skilled in the art will understand. Furthermore, since the bone plate and shaft implant of the invention are inserted into the body simultaneously, the exemplary system and method according to the invention may be more quickly and accurately positioned as compared to present systems. As will be described in greater detail below, the exemplary method according to the invention eliminates the need for impacting the bone fixation device to insert it into the bone. It should also be noted that the terms "medial" and "lateral" as used herein indicate a direction toward (medial) and away from (lateral) a midline of the body of a patient within which the bone fixation device is to be implanted. Furthermore, the terms "cranial" and "caudal" as used herein are intended to indicate a direction toward a head (cranial) and toward the feet (caudal) of the patient within which the bone fixation device is to be implanted.

Figure 10:
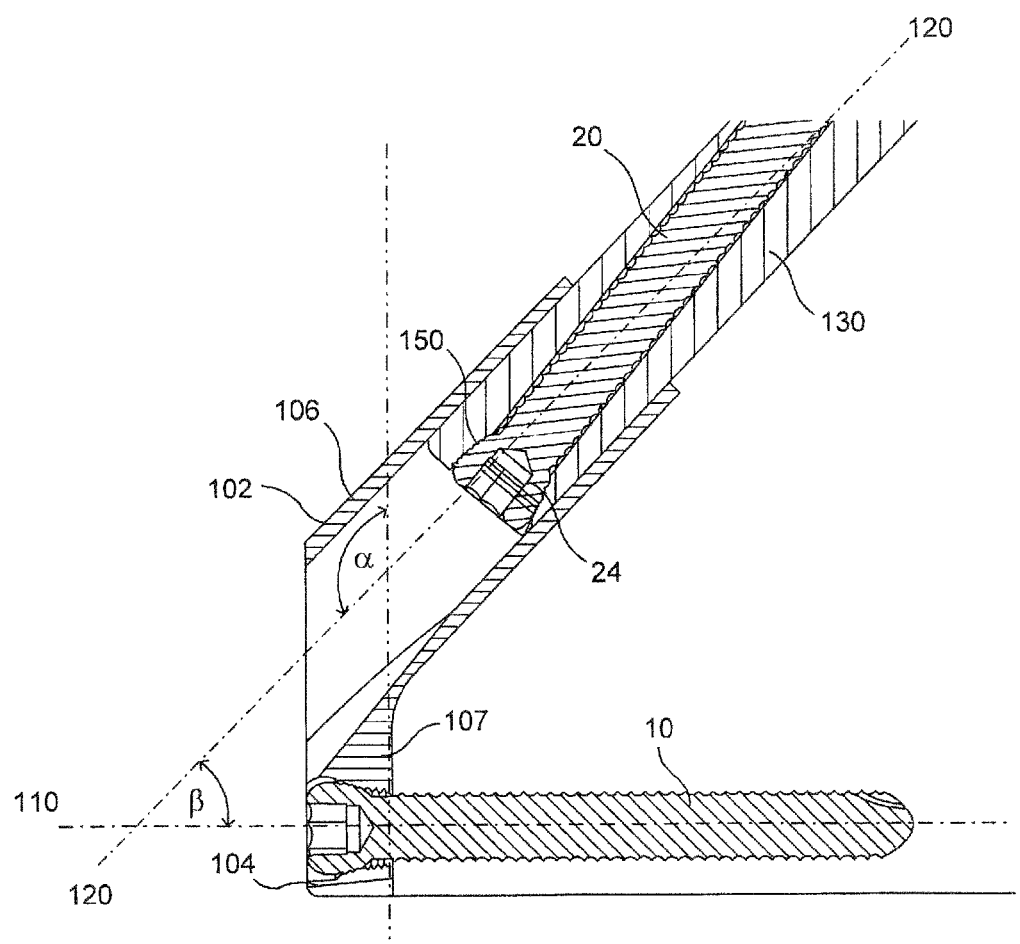
FIG. 10 shows a partial cross-sectional view of the bone fastener assembly of FIG. 1.

As shown in FIGS. 1-10, a bone fixation system 100 according to a first embodiment of the present invention comprises a bone plate 102 sized and shaped for placement on a target portion of femoral shaft opposite the femoral head (i.e., over a location through which an axis of the femoral neck passes). The bone plate 102 comprises a first portion 104 shaped to engage an outer surface of the target portion of the femur along a first portion axis parallel to an axis of the shaft of the femur and a second portion 106 extending away from the first portion along a second portion axis 120 angled with respect to the first plane at an angle selected so that, when the first portion 104 is positioned over the target portion of the femur, the second portion axis 120 extends along the axis of the femoral neck. In one exemplary embodiment, the first and second portions 104, 106 are angled such that a bone contacting surface 107 of the first portion 104 encloses an angle α of approximately 130° relative to the second portion axis 120, as shown in FIG. 10. At this angle, the second portion axis 120 encloses an angle β of approximately 40° relative to a locking hole axis 110 of a locking hole 108 extending through the plate 102. It is noted, however, that any other angle may be used as required to accommodate a patient's anatomy without deviating from the scope of the invention. For example, the angle β may be 45°. The locking hole axis 110 in this embodiment, extends substantially perpendicular to the first portion axis. However, those skilled in the art will understand that the orientation of the locking hole axis 110 may be varied as desired. The locking hole 108 includes a multi-faceted surface such as threading 112 to threadedly engage a corresponding threading on a shaft 12 of a bone fixation element 10 (e.g., a bone screw) inserted therethrough. The bone fixation element 10 may be a standard locking screw known in the art. A proximal portion of the locking hole 108 may include a non-threaded recess 114 to seat a head 14 of the bone fixation element 10 as would be understood by those skilled in the art. An outer surface of the first portion 104 may be substantially rounded such that the first portion 104 has a smooth outer profile preventing soft tissue irritation.

The second portion 106 is substantially cylindrical and extends from the first portion 104 to a distal end 116 along a length selected so that, when the first portion 104 is positioned over the target portion of the femur, the second portion 106 extends through the femoral neck to a desired position within the femoral head. A central elongated channel 118 extends through the second portion along the second portion axis 120. An outer surface of the channel is substantially smooth with the exception of an abutment 122 adjacent the distal end 116. The abutment 122 extends proximally into the channel 118 a predetermined distance and includes a proximal seat 124 and an elongated face 126. As will be described in greater detail later on, the proximal seat 124 provides a stop for an implant shaft 130 while the face 126 prevents and/or minimizes a rotation of the shaft 130 relative to the bone plate 102.

The bone fixation system 100 further comprises an implant shaft 130 for insertion through the plate 102 along the axis of the femoral neck and the second portion axis 120 into the femoral head. The shaft 130 is formed as a an elongated substantially cylindrical member extending from a proximal end 132 to a distal end 134 along a central longitudinal axis 136. A diameter of the implant shaft in this embodiment is approximately 10 mm. However, other dimensions may be used to accommodate difference in patient anatomy without deviating from the scope of the invention. In an exemplary embodiment, the distal end 134 may be blunt to prevent the implant shaft 130 from cutting through the bone 1. An outer surface of the implant shaft 130 comprises an elongated cutout 138 extending from the proximal end 132 to the distal end 134 and forming a flat surface configured to engage the face 126 of the abutment 122 preventing rotation of the shaft 130 relative to the plate 102. As those skilled in the art will understand, a shape of the cutout 138 is selected so that, when implanted, forces tending to rotate the fractured femoral head relative to the femoral shaft are countered, resulting in the femoral head being kept in a desired stable alignment with the femoral shaft. That is, the cutout 138 eliminates the need for a friction fit between the implant shaft 130 and the second portion 106 to prevent a rotation of the implant shaft 130. Any rotational force applied thereto is converted to an angled moment arm applied to the implant shaft. The cutout 138 is a portion of an outer surface of the implant shaft 130 milled or otherwise formed to define a substantially planar face which engages the face 126 in an operative configuration, as will be described in greater detail later on. A proximal end of the cutout 138 comprises a tab 140 extending radially therefrom by a distance selected to permit the tab 140 to engage the seat 124 preventing the implant shaft 130 from being inserted distally past the seat 124 defining a maximum extent by which the shaft 130 may be inserted into the bone. In an operative configuration, the implant shaft 130 engages the bone plate 102 via a form fit. As will be described in greater detail below with respect to the method of use, the form fit engagement permits lateral and medial telescoping migration of the implant shaft 130 relative to the bone plate 102 after implantation. This migration permits the implant shaft 130 to move laterally as the head of the bone moves to a corrected position during healing.

The implant shaft 130 comprises a first channel 142 extending longitudinally therethrough from the proximal end 132 to the distal end 134 in alignment with the central longitudinal axis 136. In an exemplary embodiment, the first channel 142 is dimensioned to receive a guide wire (e.g., a Kirschner wire) therethrough to guide insertion of the implant shaft 130 into the bone. The implant shaft 130 further comprises a substantially cylindrical second channel 144 extending therethrough along an axis 148 from the proximal end 132 to a distal opening 146 on a side wall of the implant shaft 130. The axis 148 in this embodiment is angled at approximately 7.5° relative to the central longitudinal axis 136. In another embodiment, the angle may be 5°, 6°, 8° or any other angle greater than 5°. In yet another embodiment, the angle may range between 0° and 5°. As shown in FIG. 8, the distal opening 146 of the second channel 144 is circumferentially separated from the cutout. Due to the angular orientation of the second channel 144 relative to the implant shaft 130, an opening of the second channel 144 at the distal opening 146 is substantially oval to permit a shaft 22 of an anti-rotation screw 20 inserted therethrough to exit therefrom. Specifically, the second channel 144 has a substantially circular cross-section. However, due to the second channel 144 exiting the implant shaft 130 at an oblique angle, as shown in FIGS. 7-9, the distal opening 146 has an oval shape. The proximal end of the second channel 144 is formed with a threaded portion 150 to threadedly engage threading formed on the shaft 22 of the anti-rotation screw 20. The threaded portion 150 may have a tapered diameter to engage a tapered diameter of a head 24 of the anti-rotation screw 20 the diameter of the threaded portion 150 being selected to prevent the head 24 from being inserted therepast.

Figure 11:
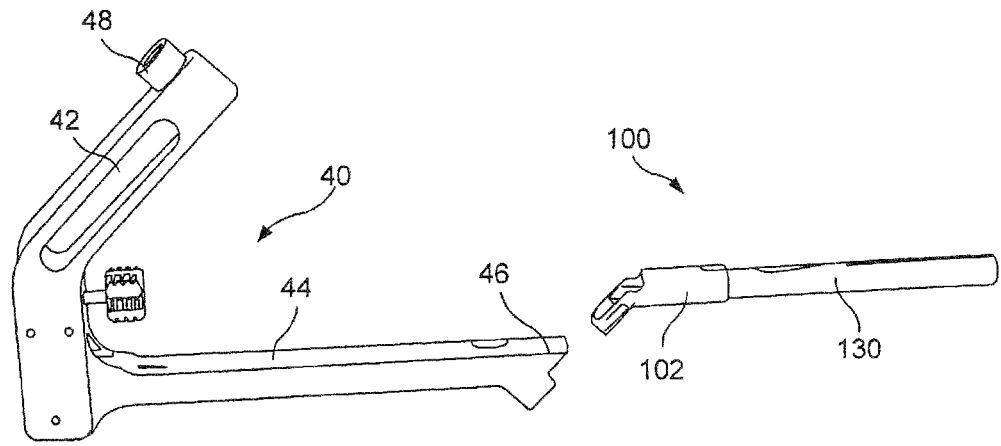
FIG. 11 shows a first surgical step for use of the bone fastener assembly of FIG. 1.
Figure 12:
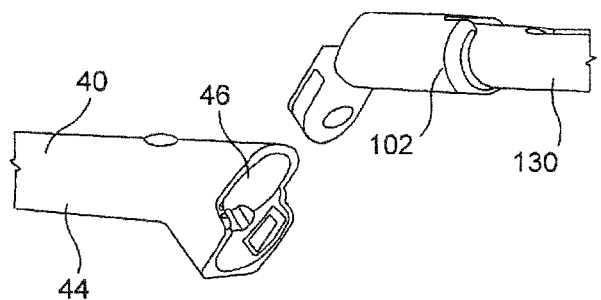
FIG. 12 shows a second surgical step for use of the bone fastener assembly of FIG. 1.
Figure 13:
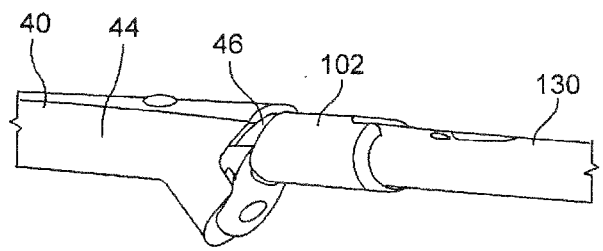
FIG. 13 shows a third surgical step for use of the bone fastener assembly of FIG. 1.
Figure 14:
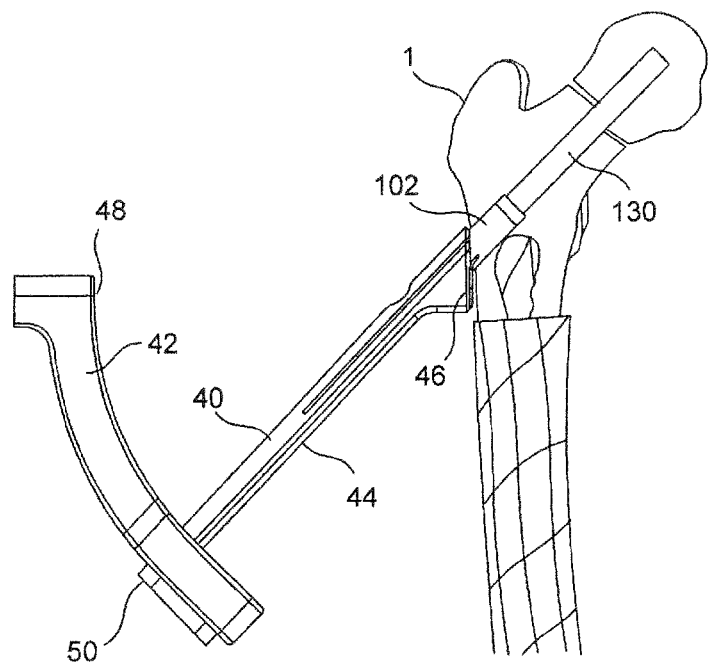
FIG. 14 shows a fourth surgical step for use of the bone fastener assembly of FIG. 1.
Figure 15:
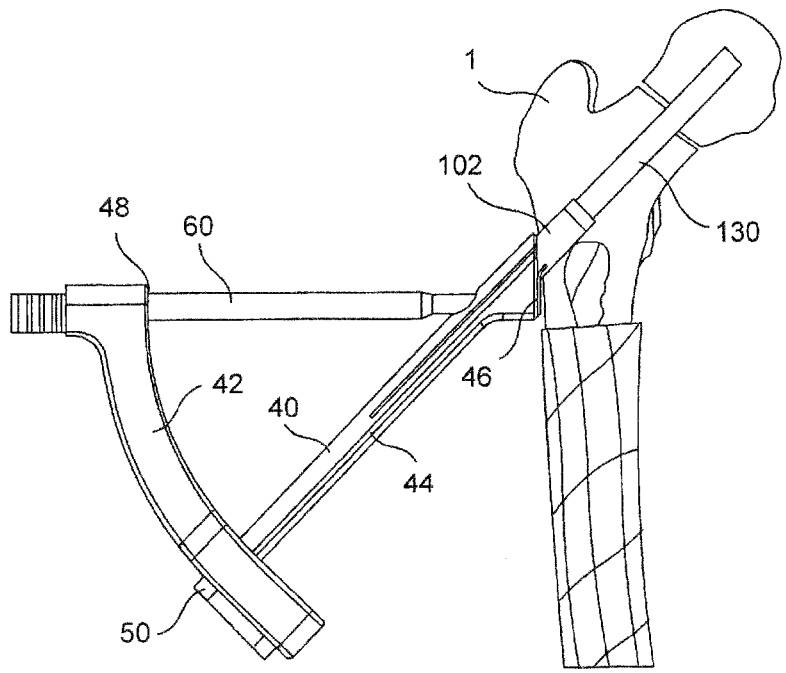
FIG. 15 shows a fifth surgical step for use of the bone fastener assembly of FIG. 1.
Figure 16:
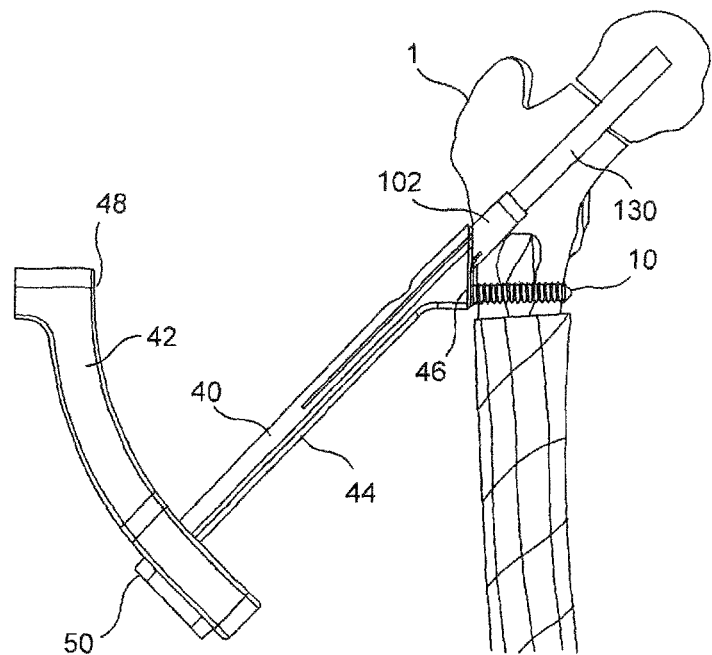
FIG. 16 shows a sixth surgical step for use of the bone fastener assembly of FIG. 1.

FIGS. 11-20 depict an exemplary method of use of the bone fixation system 100. In a first step, a patient is placed in a supine position on an operating table and the fractured bone 1 is provisionally brought into a corrected alignment via one or more of traction, abduction and internal rotation as would be understood by those skilled in the art. A straight lateral incision approximately 3-4 cm in length is made proximal to a tip of a greater trochanter. The iliotibial tract is then split lengthwise and the vastus lateralis muscle is detached dorsally from the intramuscular membrane. The proximal femoral shaft of the bone 1 is then exposed without retracting the periosteum. A guide wire is inserted through a center of the femoral head at a desired angle until a distal end of the guide wire extends into the subchondral bone, as those skilled in the art will understand. If desired one or more additional guide wires may be inserted into the femoral head as would be understood by those skilled in the art. A known reaming device (not shown) is then guided over the guide wire to ream a bore hole for the insertion of an implant according to the invention. The reamer is then removed from the bone 1 and the physician measures the appropriate implant length and selects an appropriately sized implant shaft 130. The implant shaft 130 is then inserted through the channel 118 of the second portion 106 of the bone plate 102 until engagement of the tab 140 with the seat 126 prevents further distal movement of the implant shaft 130. The assembled bone plate 102 and implant shaft 130 are then attached to an insertion instrument 40 including an arm portion 42 and an elongated shaft portion 44, a distal end 46 of which removably grasps the bone plate 102, as shown in FIGS. 11-13. It is noted that although the arm portion 42 is depicted with a curvature, any other shape may be used without deviating from the scope of the invention. The arm portion 42 includes a first opening 48 extending through a first portion at a first end thereof and a second opening 50 extending through a second portion at a second end thereof. As will be described in greater detail below, the first opening 48 according to this embodiment, has a substantially circular cross-section to permit insertion of a substantially cylindrical first protection sleeve 60 therethrough. The second opening 50 has a substantially oblong (e.g., oval, rectangular, etc.) cross-sectional shape to permit insertion of a second protection sleeve 70 therethrough, as will also be described in greater detail below. In an exemplary embodiment, the bone plate 102 is slidably inserted into engagement with the distal end 46, although other attachment mechanisms may be employed without deviating from the scope of the invention. The exemplary system 100 eliminates the need for an impactor to drive the bone plate 102 and implant shaft 130 into the bone. In an alternate embodiment, however, an impactor (not shown) may be used to first impact the implant shaft 130 into the femoral neck of a bone 1 and into the femoral head and subsequently impact the bone plate 102 into a lateral portion of the bone 1 until the plate 102 seats flush against the bone. Specifically, once the bone plate 102 has been attached to the insertion instrument 40, an impactor may be inserted through the bone plate 102 against the implant shaft 130 to impact the system 100 into the bone. The impactor (not shown) and the guide wire (not shown) may then be removed from the bone, leaving the insertion instrument 40 and system 100 positioned in the bone, as shown in FIG. 14.

A first protection sleeve 60 is then inserted through the first opening 48 in the insertion instrument 40. The first protection sleeve 60 may extend through the first opening 48 and into the distal end 46 of the insertion instrument 40 at a predetermined angle relative to the angle of the elongated shaft portion 44. In an exemplary embodiment, the first protection sleeve 60 and elongated shaft 44 enclose an angle of approximately 40°, although other angles may be used without deviating from the scope of the invention. The first protection sleeve 60 guides the drilling of a hole into the bone 1 to permit insertion of the bone fixation element 10 (i.e., a bicortical shaft screw) therein. Specifically, a drilling mechanism known in the art may be inserted through the first protection sleeve 60 to drill an opening through the locking hole 108 of the bone plate 102 and into the bone 1. The drilling mechanism may then be removed and the bone fixation element 10 may be inserted through the first protection sleeve 60 and bone plate 102 and into the bone 1. Dimensions of the bone fixation element 10 are selected to permit bicortical insertion thereof through the bone 1, as those skilled in the art will understand. The first protection sleeve 60 may then be removed from the insertion instrument, leaving the bone fixation element 10 in place within the bone 1.

Figure 17:
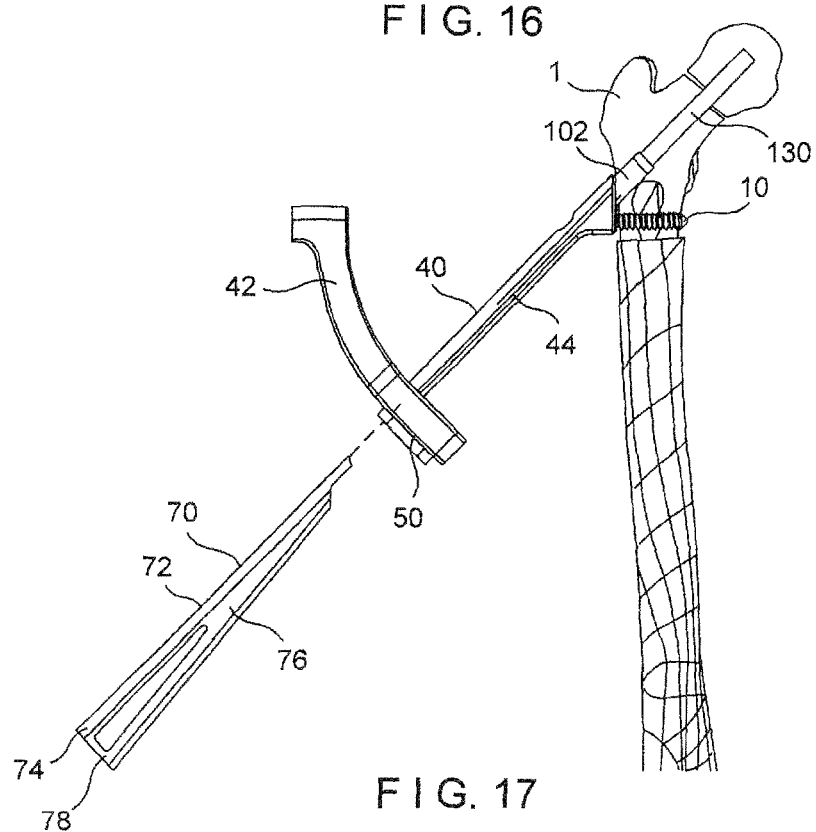
FIG. 17 shows a seventh surgical step for use of the bone fastener assembly of FIG. 1.
Figure 18:
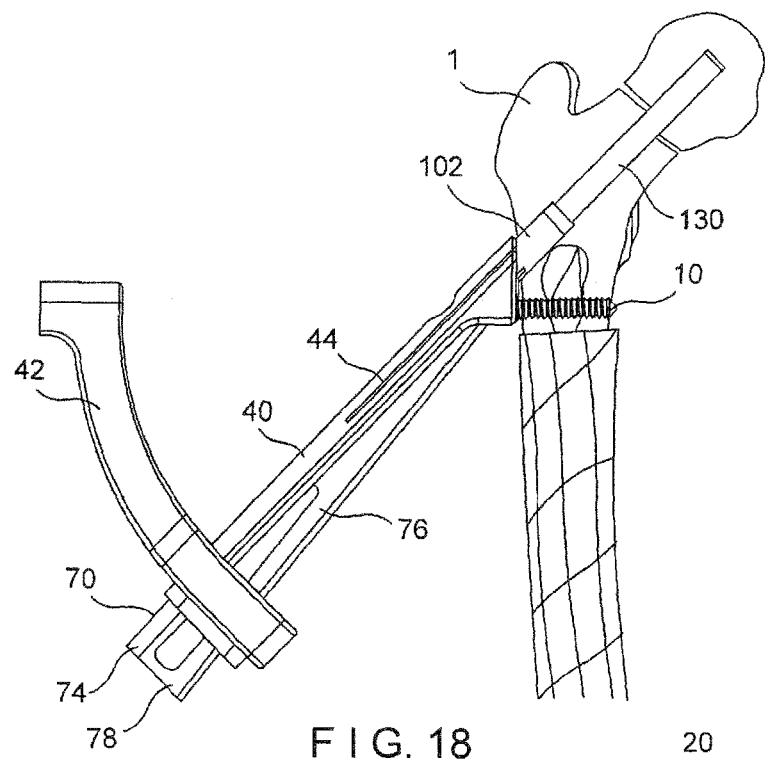
FIG. 18 shows an eighth surgical step for use of the bone fastener assembly of FIG. 1.
Figure 19:
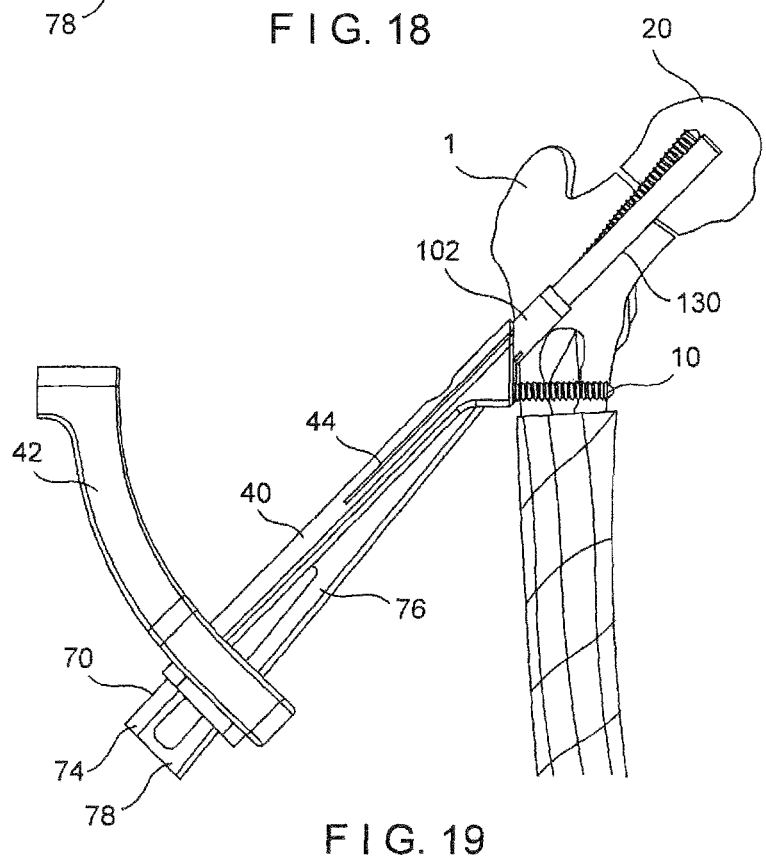
FIG. 19 shows a ninth surgical step for use of the bone fastener assembly of FIG. 1.

As shown in FIGS. 17-18, the second protection sleeve 70 may comprise a first elongated shaft portion 72 having a first channel 74 extending therethrough, the first elongated shaft portion 72 being insertable through the insertion instrument. In an operative configuration, a longitudinal axis 75 of the first channel 74 is substantially aligned with the longitudinal axis 136 of the implant shaft 130. The second protection sleeve 70 further comprises a second elongated shaft portion 76 having a second channel 78 extending therethrough, a longitudinal axis of the second elongated shaft portion 76 being offset from the longitudinal axis 75 by approximately 5° to align with the axis 148 of the implant shaft 130, as described in greater detail earlier and depicted in FIG. 9. The elongated shaft 44 may comprise an elongated slot (not shown) on a side wall thereof to permit insertion of second protection sleeve 70 to the position depicted in FIG. 18.

Figures 21, 23:
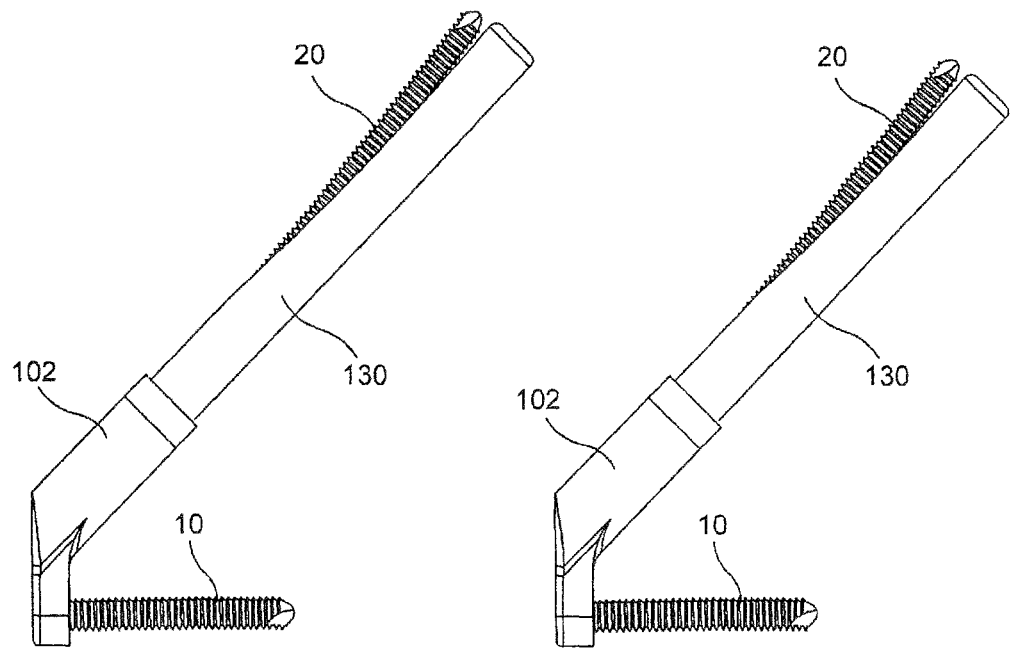
FIG. 21 shows a side view of the bone fastener assembly of FIG. 1 in a first post-operative configuration.
FIG. 23 shows a side view of the bone fastener assembly of FIG. 1 in a second post-operative configuration.
Figures 22, 24:
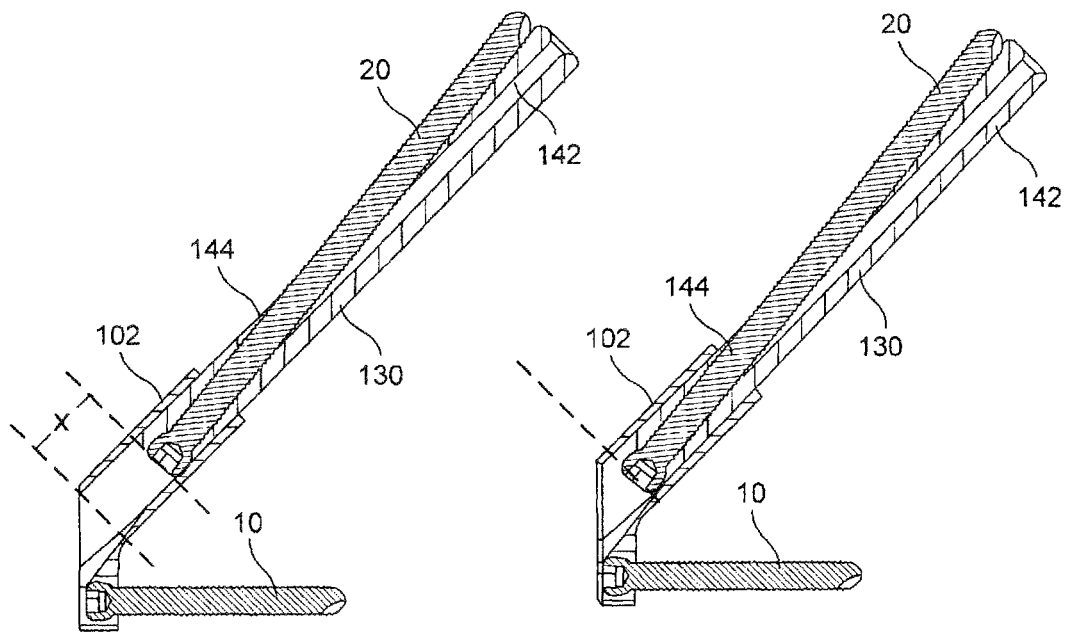
FIG. 22 shows a cross-sectional view of the bone fastener assembly of FIG. 21.
FIG. 24 shows a cross-sectional view of the bone fastener assembly of FIG. 23.

Once the second protection sleeve 70 has been seated against the proximal end 132 of the implant shaft 130, a drilling mechanism (not shown) may be inserted through the second channels 78 and 144 to prepare the bone 1 for the anti-rotation bone screw 20. As those skilled in the art will understand, in softer bone, pre-drilling may not be necessary. As would be understood by those skilled in the art, a driving mechanism (not shown) may then be used to insert the anti-rotation screw 20 through the second protection sleeve 70 and implant shaft 130 and into the bone 1. The second protection sleeve 70 and insertion instrument 40 may then be removed from the body, leaving the system 100 implanted in the bone 1. Once implanted, the head of the femur is prevented from rotation relative to the bone 1 via the anti-rotation screw 20 and bone plate 102. The shaft 130 is permitted to migrate within a desired range relative to the bone plate 102. Specifically, the combined implant shaft 130 and bone fixation element anti-rotation screw 20 inserted therethrough are capable of migrating a distance x from the configuration of FIGS. 21-22 to the configuration of FIGS. 23-24. Those skilled in the art will understand that this migration of the implant shaft 130 relative to the bone plate 102 minimizes the risk of medial perforation of the implant shaft 130 through the femoral head after implantation and as the bone heals.

It is noted that although the exemplary method depicts the insertion of the bicortical screw 10 first, followed by the insertion of the anti-rotation screw 20, the order of insertion may be changed without deviating from the scope of the invention to suit, for example, a surgeon's preference. For example, the method of insertion for the system 800 as described below is directed to the insertion of an anti-rotation screw first, followed by a bi-cortical screw.

Figure 25:
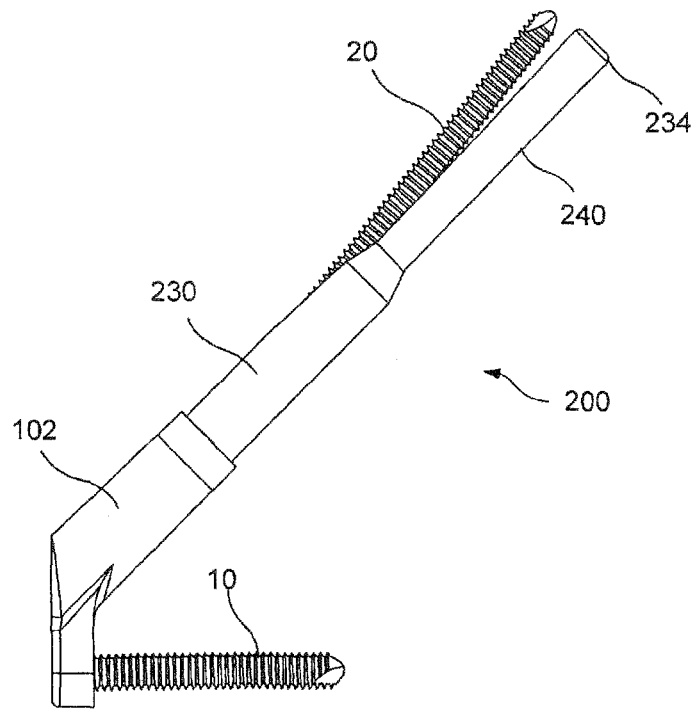
FIG. 25 shows a side view of a bone fastener assembly according to a first alternate embodiment of the invention.
Figure 26:
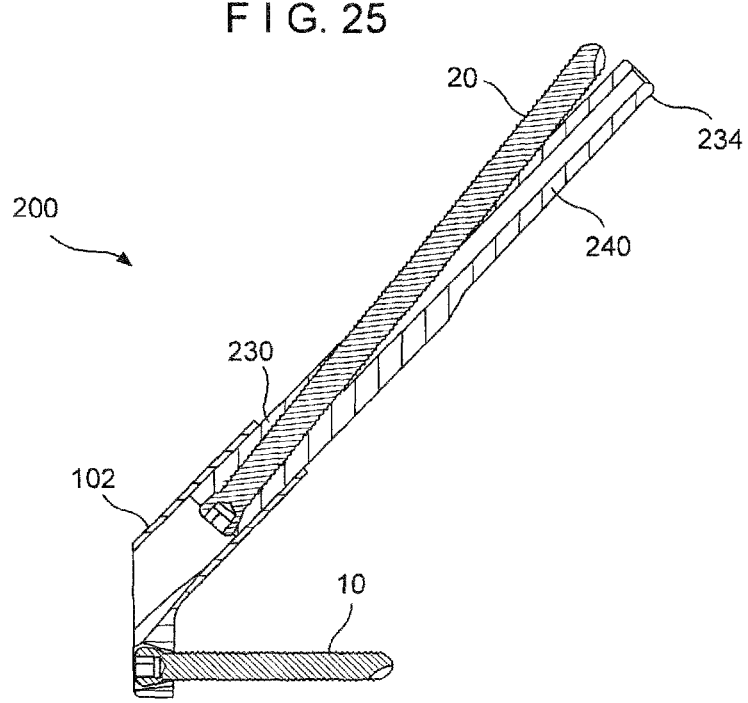
FIG. 26 shows a cross-sectional view of the bone fastener assembly of FIG. 25.

FIGS. 25-26 depict a system 200 according to a first alternate embodiment according to the invention. The system 200 is formed substantially similarly to the system 100, wherein like elements have been referenced with like reference numerals. The system 200 comprises a bone plate 102 and an implant shaft 230. The implant shaft 230 is formed substantially similarly to the implant shaft 130 with the exception of a reduced diameter distal portion 240. The implant shaft 230 extends from the proximal end 132 to the distal end 234. The reduced diameter distal portion 240 extends proximally from the distal end 134 a predetermined distance. As those skilled in the art will understand, the reduced diameter portion 240 reduces the amount of bone removal needed for insertion of the implant shaft 230 into the bone and has a wider spread between the distal end 234 of the implant shaft 230 and distal end of the anti-rotation screw 20.

Figure 27:
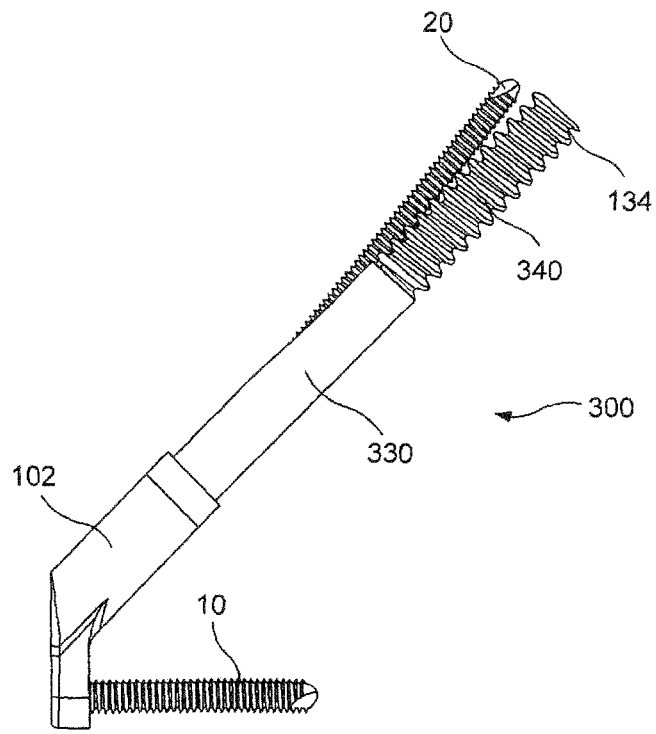
FIG. 27 shows a side view of a bone fastener assembly according to a second alternate embodiment of the invention.
Figure 28:
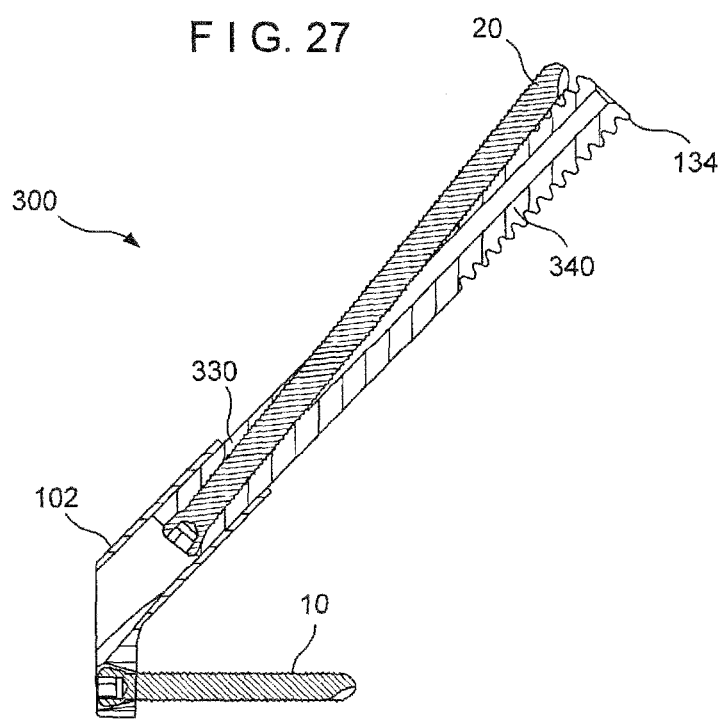
FIG. 28 shows a cross-sectional view of the bone fastener assembly of FIG. 27.

FIGS. 27-28 depict a system 300 according to a second alternate embodiment according to the invention. The system 300 is formed substantially similarly to the system 100, wherein like elements have been referenced with like reference numerals. The system 300 comprises a bone plate 102 and an implant shaft 330 formed substantially similarly to the implant shaft 130 with the exception of a threaded distal portion 340. The implant shaft 330 extends from a proximal end 132 to a distal end 234 with the threaded distal portion 340 extending proximally from the distal end 134 a predetermined distance. As those skilled in the art will understand, the threaded distal portion 340 aids in retention of the implant shaft 330 within the bone 1.

Figure 29:
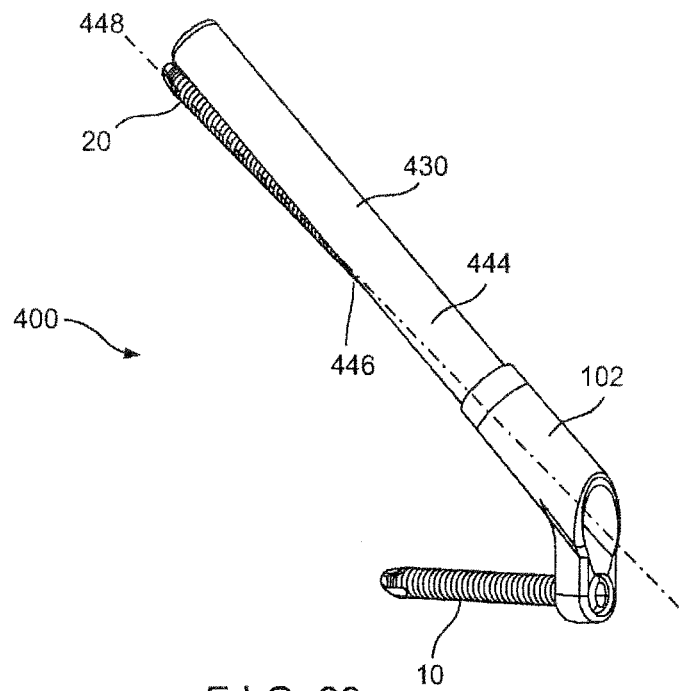
FIG. 29 shows a perspective view of a bone fastener assembly according to a third alternate embodiment of the invention.

FIG. 29 depicts a system 400 according to a third alternate embodiment according to the invention. The system 400 is formed substantially similarly to the system 100, wherein like elements have been referenced with like reference numerals. The system 400 comprises a bone plate 102 and an implant shaft 430. The implant shaft 430 is formed substantially similarly to the implant shaft 130 with the exception of a position and angle of a channel 444 extending therethrough. Specifically, the channel 144 of the system 100 extends from the proximal end 132 to a distal opening 146 positioned on a cranial surface of the implant shaft in an operative configuration. In contrast, the channel 444 extends from the proximal end 132 to a distal end 446 positioned on a caudal surface of the implant shaft 430 in an operative configuration. A channel axis 448 of the channel 444 is angled at approximately −5° relative to the central longitudinal axis 136. However, those skilled in the art will understand that this angle may vary as desired without departing from the scope of the invention.

Figure 30:
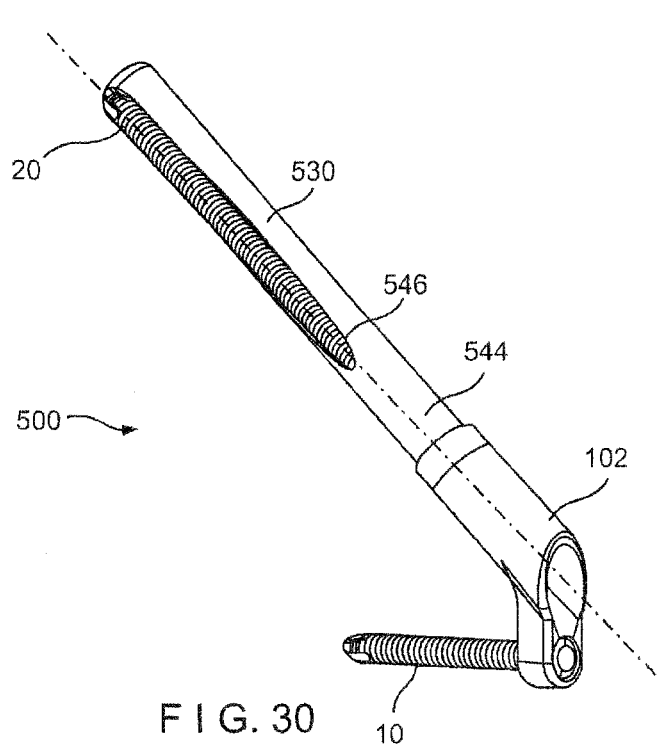
FIG. 30 shows a perspective view of a bone fastener assembly according to a fourth alternate embodiment of the invention.

FIG. 30 depicts a system 500 according to a fourth alternate embodiment according to the invention. The system 500 is formed substantially similarly to the system 100, wherein like elements have been referenced with like reference numerals. The system 500 comprises a bone plate 102 and an implant shaft 530 formed substantially similarly to the implant shaft 130 with the exception of a position and angle of a channel 544 extending therethrough. Specifically, the channel 544 extends from the proximal end 132 to a distal end 546 positioned on a surface of the implant shaft 530 which, in an operative configuration, faces one of an anterior and a posterior direction. A physician may determine which of the systems 100, 400 and 500 to use in accordance with, for example, a size and location of a fracture in the bone, as those skilled in the art will understand.

Figure 31:
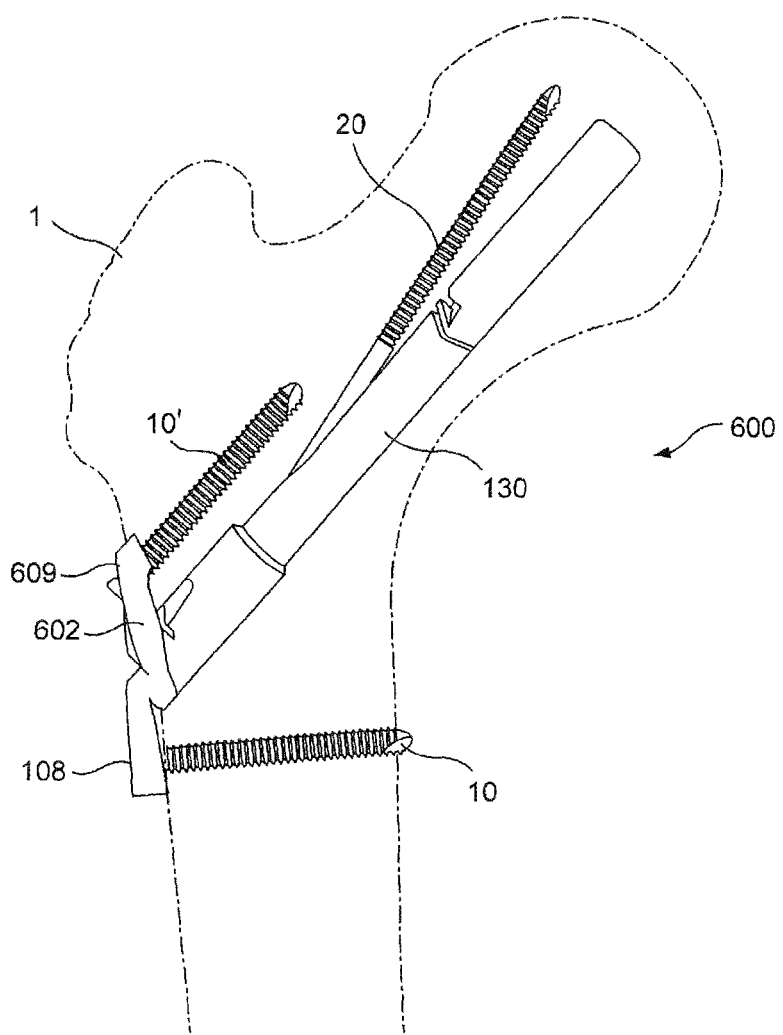
FIG. 31 shows a perspective view of a bone fastener assembly according to a fifth embodiment of the invention.
Figure 32:
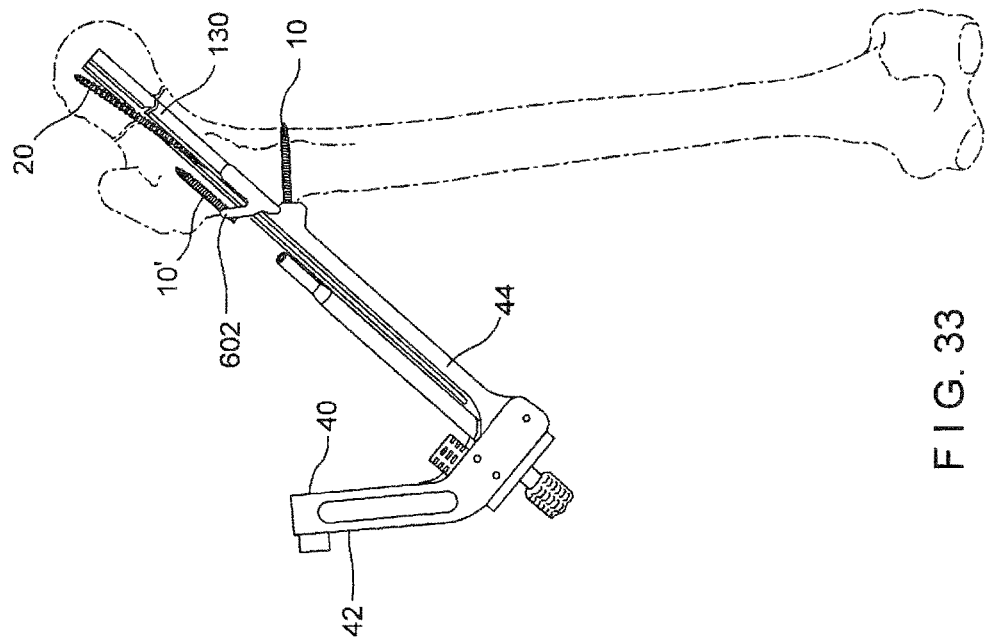
FIG. 32 shows a first surgical step for use of the bone fastener assembly of FIG. 31.
Figure 33:
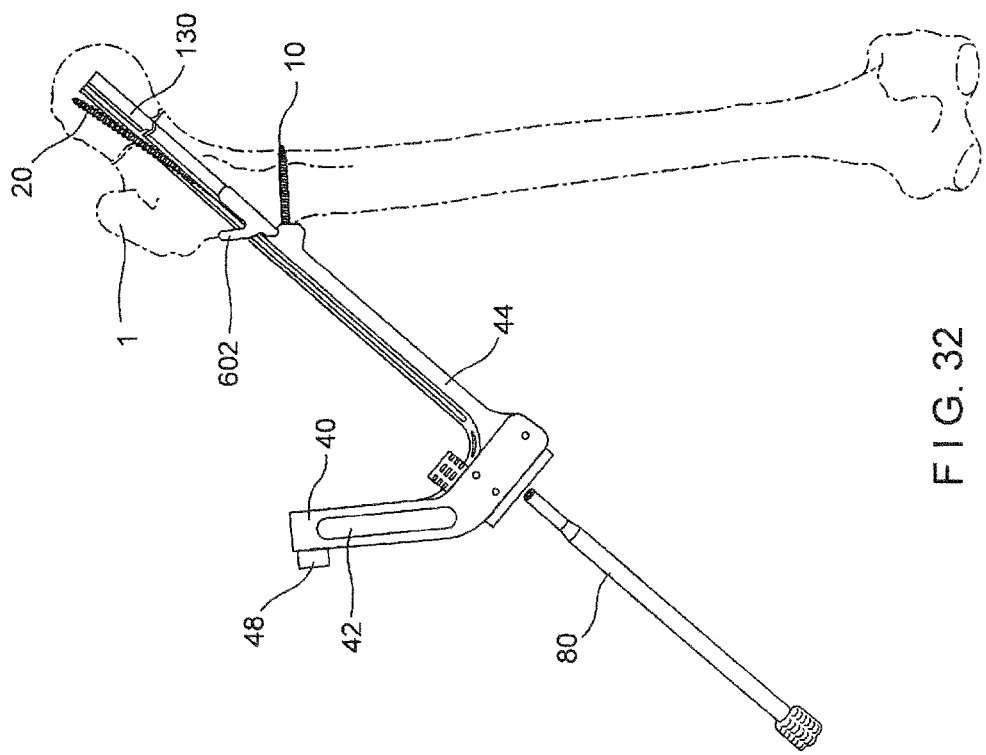
FIG. 33 shows a second surgical step for use of the bone fastener assembly of FIG. 31.

FIGS. 31-33 depict a system 600 according to a fifth alternate embodiment according to the invention. The system 600 is formed substantially similarly to the system 100, wherein like elements have been referenced with like reference numerals. The system 600 comprises a bone plate 602 and the implant shaft 130, bone plate 602 being formed substantially similarly to the implant shaft 130 with the exception of an additional locking hole extending therethrough. Specifically, the bone plate 602 comprises a central longitudinal channel 118. A first locking hole 608 is positioned caudally of the central longitudinal channel 118 and is substantially similar to the locking hole 108. A second locking hole 609 extends through the bone plate 602 cranially of the central longitudinal channel 118. A hole axis of the second locking hole is substantially parallel to the channel axis 120 of the central longitudinal channel 118 such that a bone fixation element 10' inserted therethrough does not intersect any other portion of the system 600.

An exemplary insertion method for the system 600 is substantially similar to the method disclosed earlier with respect to system 100. However, once the first and second bone fixation elements 10, 20 have been inserted, a third drill sleeve 80 is inserted through the insertion instrument 40 to align with the second locking hole. A drilling mechanism (not shown) is inserted through the drill sleeve 80 and into the bone to define the trajectory of the bone fixation element 10'. A driving mechanism (not shown) is then inserted through the drill sleeve 80 to screw the bone fixation element 10' into the bone 1. The exemplary system 600 provides added structural support to the bone 1 and may be particularly advantageous in bones with multiple fractures or otherwise weaker bones.

Figure 34:
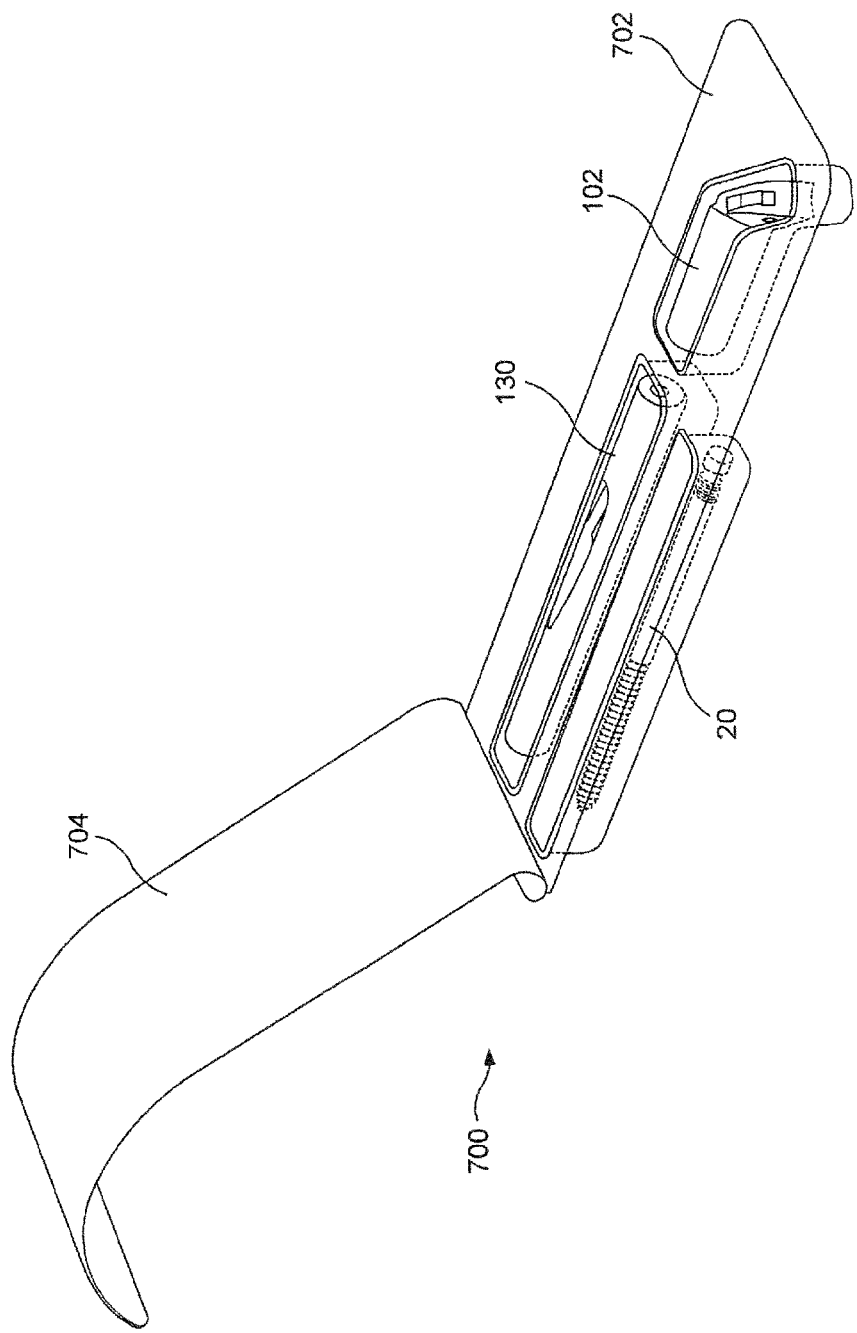
FIG. 34 shows a first embodiment of a kit for packaging any of the bone fastener assemblies according to the invention.

As shown in FIG. 34, the systems 100, 200, 300, 400, 500 and 600 may be manufactured and packaged as a kit 700 including the bone plate 102, 602, implant shaft 130, 230, 330, 430, 530, and anti-rotation screw 20 along with instructions for implantation as described above. The implant shaft 130, 230, 330, 430, 530 and anti-rotation screw 20 may be provided in corresponding dimensions to one another. The kit may be sold in various implant shaft lengths to suit the requirements of a particular procedure. The bone fixation element 10 may be offered separately. The kit 700 may include a molded packaging 702 formed of plastic or another suitable material having a removable seal 704 provided thereover, the seal 704 maintaining the sterility of the system.

Figure 35:
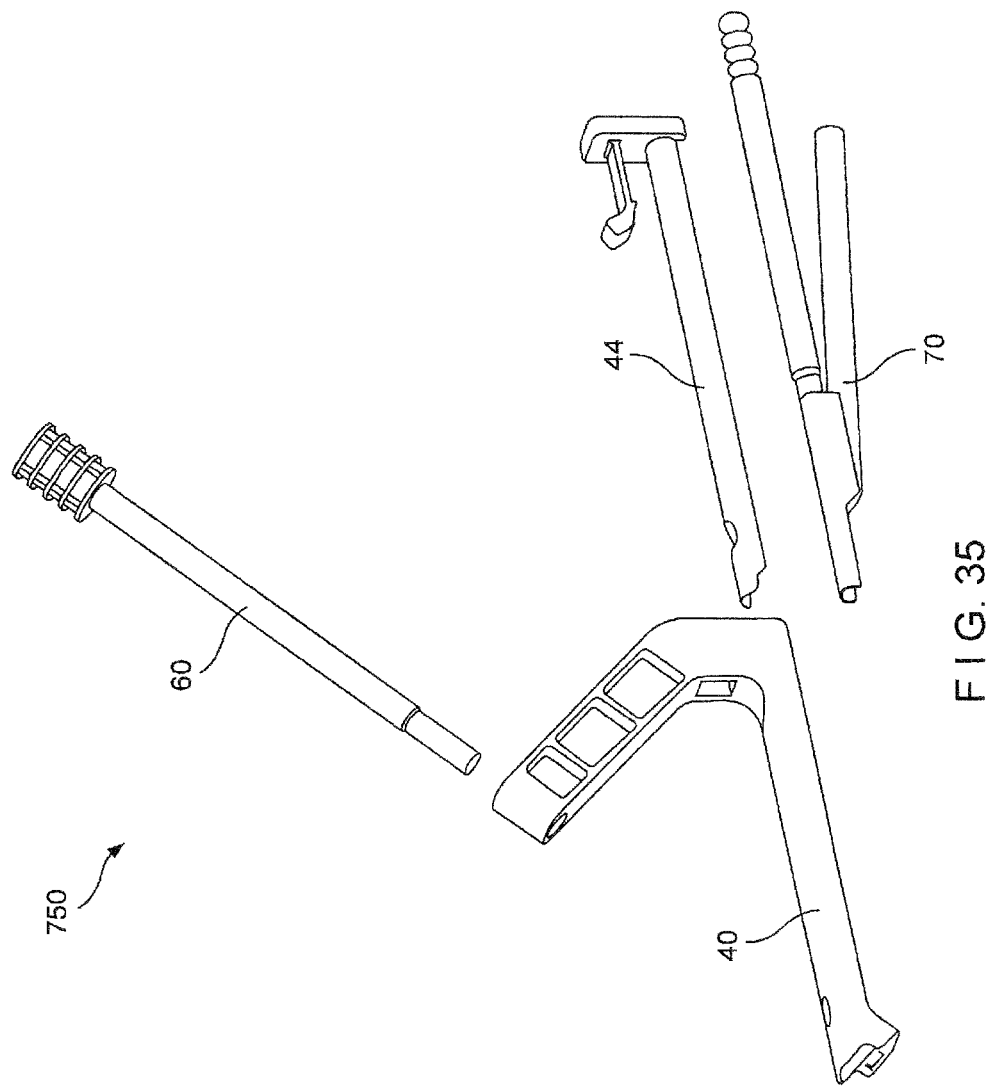
FIG. 35 shows a second embodiment of a kit for insertion devices for use with the bone fastener according to the invention.
Figure 36:
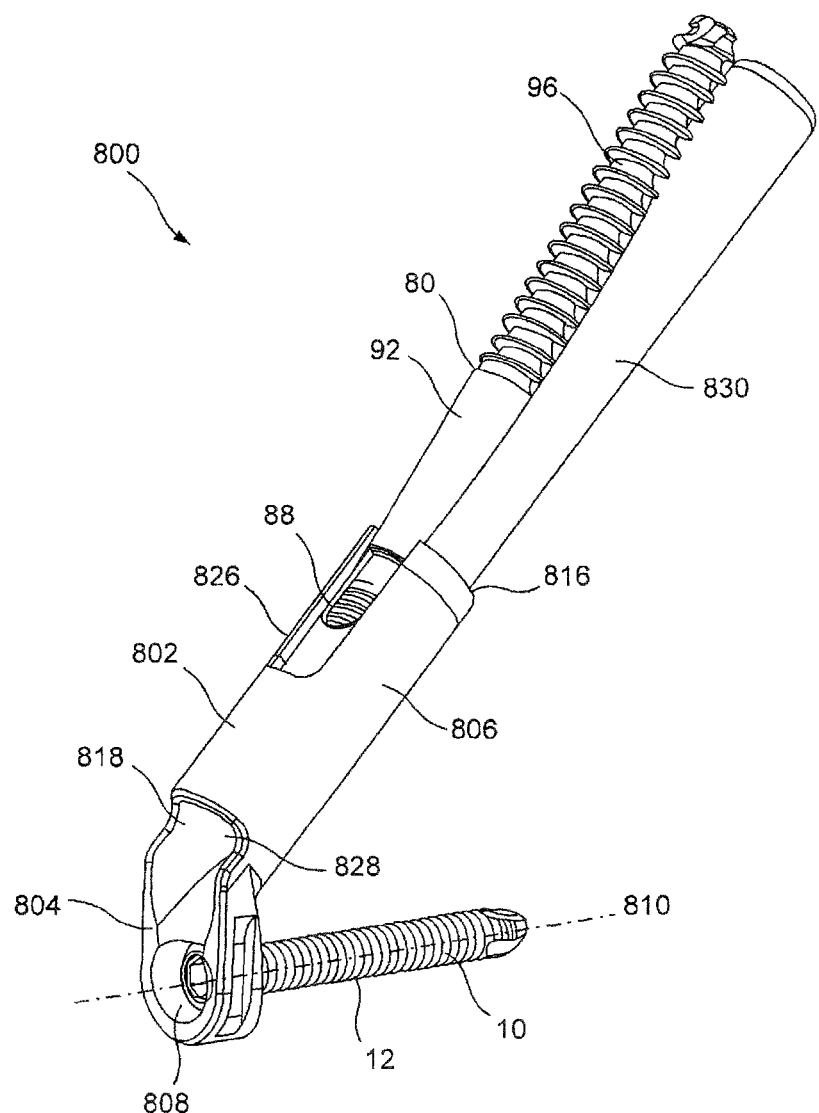
FIG. 36 shows a perspective view of a bone fastener assembly according to another embodiment of the invention.
Figure 37:
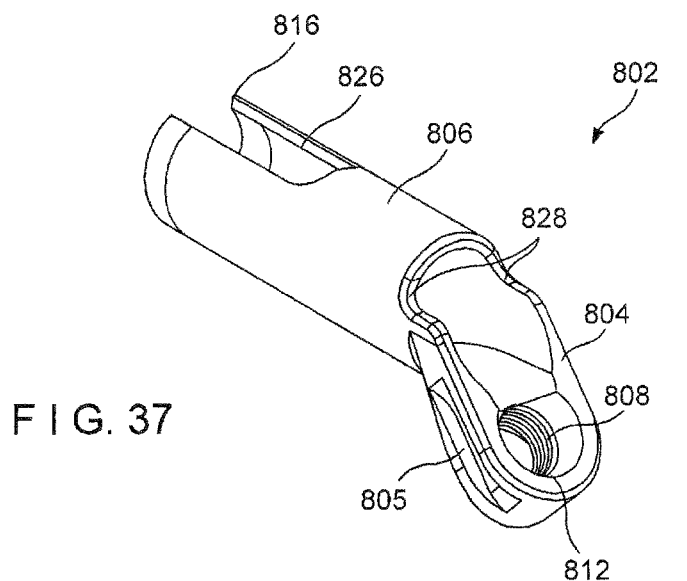
FIG. 37 shows a first perspective view of a bone plate of the bone fastener assembly of FIG. 36.
Figure 38:
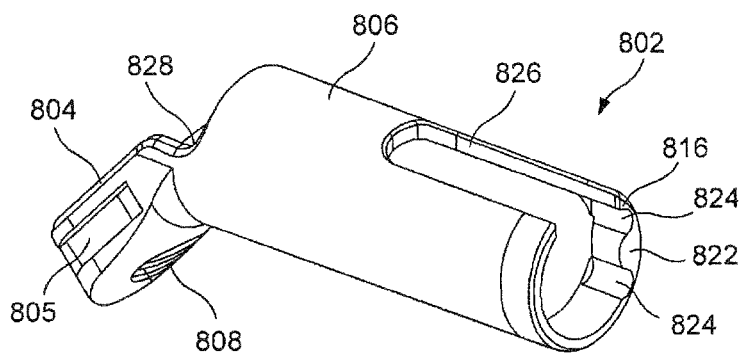
FIG. 38 shows a second perspective view of the bone plate of FIG. 36.
Figure 39:
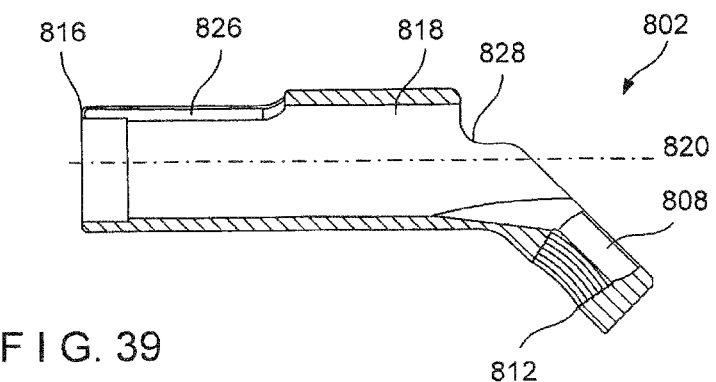
FIG. 39 shows a cross-sectional view of the bone plate of FIG. 36.
Figure 40:
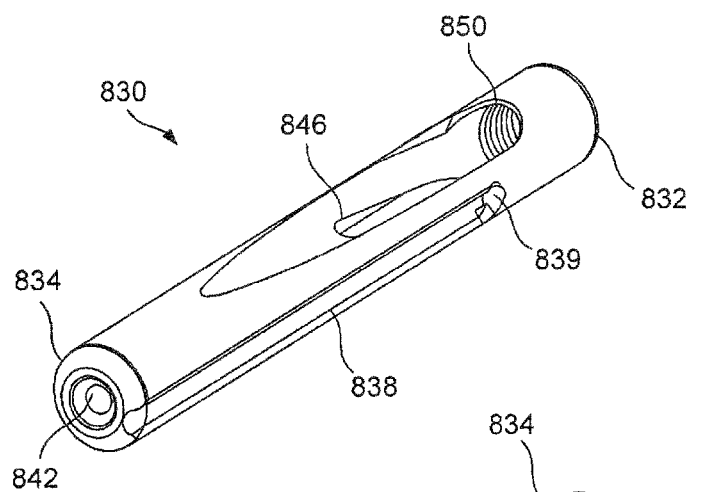
FIG. 40 shows a first perspective view of an implant shaft of the bone fastener assembly of FIG. 36.
Figure 41:
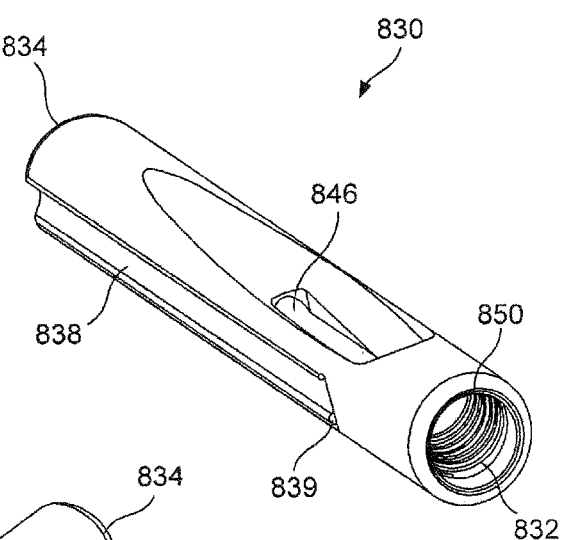
FIG. 41 shows a second perspective view of the implant shaft of FIG. 40.
Figure 42:
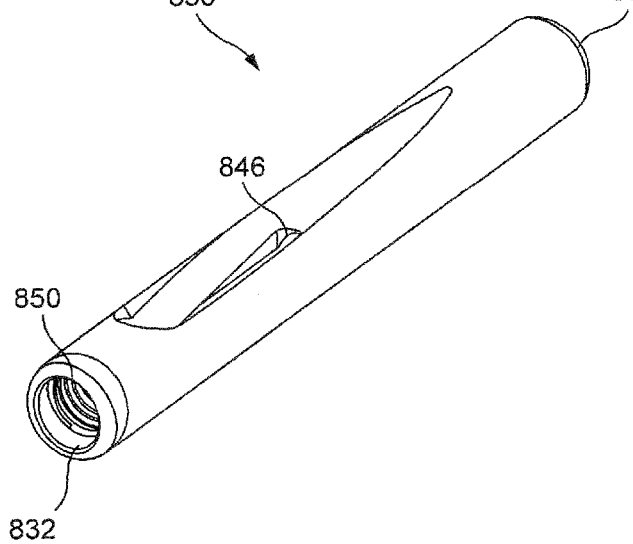
FIG. 42 shows a third perspective view of the implant shaft of FIG. 40.

FIG. 35 depicts a single-use kit for the instruments required for the completion of a bone fixation procedure according to the invention, as described above with respect to the exemplary method of use for the system 100. A kit 750 according to the invention may include the insertion instrument 40, the corresponding removable shaft portion 44 and the first and second protection sleeves 60, 70. In an operative configuration, the removable shaft portion 44 is attached to an elongated shaft 46, which is further attached to the second protection sleeve 70 via a Y-connector. A side wall of the insertion instrument 40 includes a slot (not shown) permitting insertion of the Y-connector therepast. The removable shaft portion 44 further comprises a tab 48 including a protruding distal end 49 extending radially away therefrom. In an operative configuration, the tab 48 is received through the second opening 50 with a snap-fit engagement. Specifically, the tab 48 is deformed radially inward when being inserted through the second opening 50. Once moved thereinto, the tab 48 moves radially outward to assume its initial configuration so that the protruding distal end 49 is received within a corresponding portion of the second opening 50, thus locking the shaft portion 44 to the instrument 40. The insertion instrument 40 may be made of a low-cost plastic injection molding while the protection sleeves 60, 70 and shaft portion 44 may be formed of a low-cost metal injection molding. In another embodiment, the insertion instrument 40 may be made of standard parts (e.g., standard tubing, etc.) connected to form the depicted structure. The kit 750 may be sold as a single unit for use with any of the exemplary systems 100, 200, 300, 400, 500, 600, 800 disclosed herein.

FIGS. 36-50 depict a system 800 according to another alternate embodiment according to the invention. The system 800 is formed substantially similarly to the system 100, wherein like elements have been referenced with like reference numerals. The system 800 comprises a bone plate 802 and an implant shaft 830. The implant shaft 830 is formed substantially similarly to the implant shaft 130 with the exception of the structural differences noted below.

Figure 45:
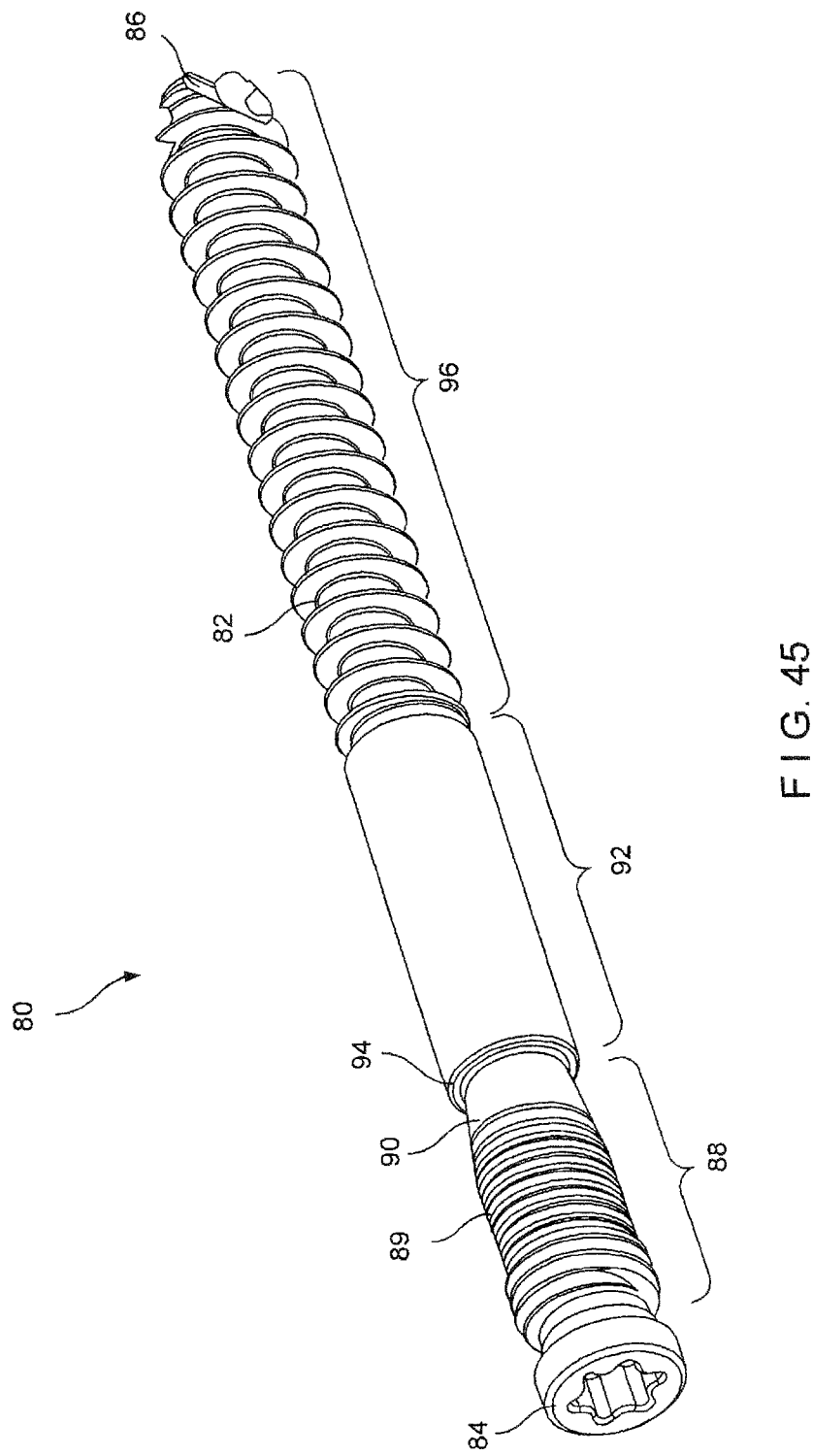
FIG. 45 shows a perspective view of an anti-rotation screw of the bone fastener assembly of FIG. 37.
Figure 46:
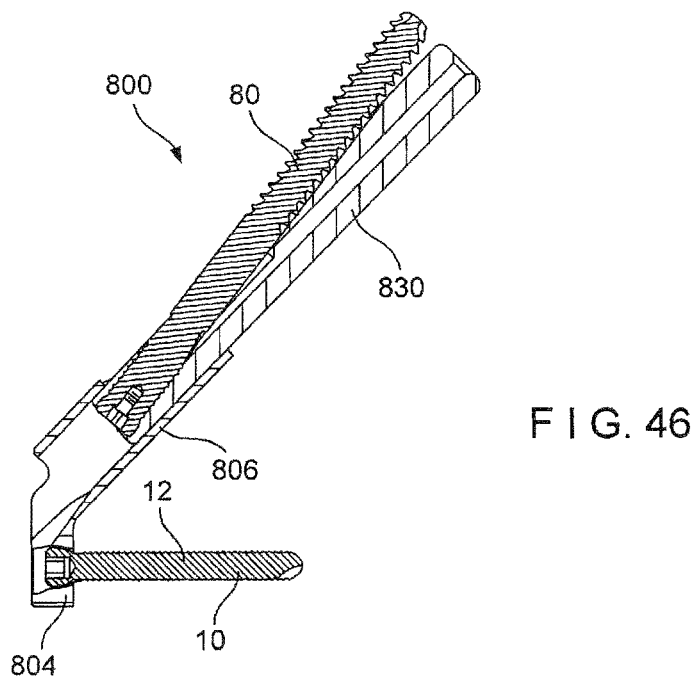
FIG. 46 shows a first surgical step for use of the bone fastener assembly of FIG. 36.
Figure 47:
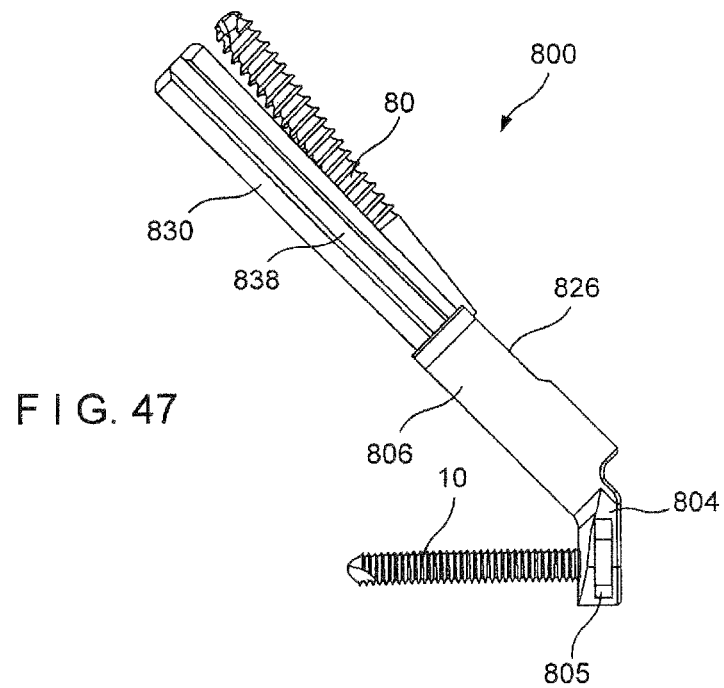
FIG. 47 shows a second surgical step for use of the bone fastener assembly of FIG. 36.

The bone plate 802 comprises a first portion 804 shaped to engage an outer surface of the target portion of the femur along a first portion axis parallel to an axis of the shaft of the femur and a second portion 806 extending away from the first portion along a second portion axis angled with respect to the first plane at an angle selected so that, when the first portion is positioned over the target portion of the femur, an axis of the second portion extends along the axis of the femoral neck. The first portion 804 comprises a locking hole 808 extending through the plate 802 along a locking hole axis 810 which extends substantially perpendicular to a first portion axis. The locking hole 808 is formed substantially similar to the locking hole 108 of the system 100 and may include a multi-faceted surface such as threading 812 to threadedly engage a corresponding threading on the shaft 12 of the bone fixation element 10 (e.g., a bone screw) inserted therethrough. An outer surface of the first portion 804 is substantially rounded such that the first portion 804 has a smooth outer profile substantially matching that of the target portion of the femur. The outer surface of the first portion 804 further comprises one or more recesses 805 configured and dimensioned to permit grasping of the bone plate 802 by the insertion instrument 40, as will be described in greater detail with respect to the exemplary method below. The recess 805 may extend substantially parallel to an axis of the first portion 804. In an exemplary embodiment, first and second recesses 805 may be provided on opposing walls of the first portion 804 to permit grasping of the bone plate 802. Dimensions of each of the recesses may be selected to conform to the dimensions of a gripping portion of the implant holder The second portion 806 is substantially cylindrical and extends from the first portion 804 to a distal end 816. A central elongated channel 818 extends through the second portion along a second portion axis 820. An outer surface of the channel 818 is substantially smooth with the exception of an abutment 822 adjacent the distal end 816. The abutment 822 extends radially into the channel 818 a predetermined distance and is bordered on both sides by grooves 824. A cutout 826 extends proximally from the distal end 816 of the second portion. In an exemplary embodiment, the cutout 826 is substantially rectangular with rounded corners and is open to the distal end 816. The cutout 826 is positioned so that, in an operative configuration, the cutout faces a cranial direction. Dimensions of the cutout 826 may be selected to permit the anti-rotation screw 80 to extend therefrom, as shown in FIGS. 35 and 45-46. That is, the cutout 826 prevents the need for advancement of the implant shaft 830 out of the bone plate 102 beyond a threshold distance. Rather, in smaller bones, the implant shaft 830 may extend out of the bone plate 802 by only a minimal required distance, with a distal end 846 of the second channel 844 be housed within the second portion 806. In an operative configuration, the anti-rotation screw 80 may be inserted through the implant shaft 830 to extend out of the cutout 826. As those skilled in the art will understand, the cutout 826 may be formed with any length to permit use of the system 800 in bones having varying dimensions. Furthermore, for use in longer bones, the cutout 826 may optionally be omitted. Furthermore, the cutout 826 allows telescoping of the implant shaft 830 relative to the bone plate 802.

The second portion 806 further comprises first and second recesses 828 provided on opposing walls adjacent a proximal end of the channel 818. The first and second recesses are configured and dimensioned to permit insertion of a corresponding portion of a locking core therethrough to guide insertion of the bone plate 802 over the bone, as will be described in greater detail below.

The implant shaft 830 is formed as a an elongated substantially cylindrical member extending from a proximal end 832 to a substantially blunt distal end 834 along a central longitudinal axis 836. An outer surface of the implant shaft 830 comprises an elongated cutout 838 extending from a proximal end 839 to the distal end 834, the cutout 838 have a shape corresponding to the shape of the abutment 822 and grooves 824 to permit engagement therewith. As described in greater detail with respect to the system 100, this engagement prevents rotation of the shaft 830 relative to the plate 802. As those skilled in the art will understand, engagement of the abutment 822 with the proximal end 839 of the cutout 838 prevents the shaft 130 from extending distally out of the plate 802, defining a maximum extent by which the shaft 830 may be inserted into the bone. Furthermore, due to the hemispherical shape of the cutout 838, a rotational force applied to the implant shaft 830 after implantation is converted to a substantially perpendicular moment arm, preventing wedging of the implant shaft 830 against walls of the second portion 806. The prevention of the wedging of the implant shaft 830 also prevents high-friction forces that may influence the ability of the implant shaft 830 to telescope relative to the plate 802.

The implant shaft 830 comprises a first channel 842 extending longitudinally therethrough from the proximal end 832 to the distal end 834 in alignment with a central longitudinal axis 836. The first channel 842 is dimensioned to receive a guide wire (e.g., a Kirschner wire) therethrough to guide insertion of the implant shaft 830 into the bone. The implant shaft 830 further comprises a second channel 844 extending therethrough along an axis 848 from the proximal end 132 to a distal opening 846 on a side wall of the implant shaft 830, the distal opening 846 being circumferentially separated from the cutout 838. The distal opening 846 is substantially oval to permit a shaft 82 of an anti-rotation screw 80 inserted therethrough to exit therefrom. Similar to the distal opening 146, the distal opening 846 is oval due to an oblique position of the substantially circular second channel 844 relative to the implant shaft 830. The proximal end of the second channel 844 includes threading 850 to threadedly engage threading formed on the shaft 82 of the anti-rotation screw 80, as will be described in greater detail below. Whereas the threading 150 of the implant shaft 130 is substantially tapered, the threading 850 is substantially cylindrical.

The anti-rotation screw 80 extends from a head 84 at a proximal end and along the shaft 82 to a distal end 86. The shaft 82 includes a first portion 88 having a first outer diameter selected to permit engagement with the threading 850 of the implant shaft 830. Specifically, the first portion 88 includes a first threaded region 89 including a double-lead thread to aid in engagement thereof with the threading 850. The first portion 88 also includes a non-threaded tapered region 90 shaped to allow telescoping of the anti-rotation screw 80 when inserted into a target orientation in the bone. The first portion 88 preferably has a substantially tapered shape corresponding to a tapered shape of the second channel 844. A second non-threaded portion 92 extends distally from the first portion 88. A diameter of the second portion 92 is greater than a diameter of the tapered region 90, forming a telescoping stop 94 at a junction thereof. In an operative configuration, the second portion 92 extends out of the implant shaft 830 and into the bone. A third threaded portion 96 extends distally from the second non-threaded portion 94 and includes single lead spongiosa threading configured to engage bone in an operative configuration, as will be described in greater detail with respect to the exemplary method below. As those skilled in the art will understand, the double-lead thread of the first threaded region 89 matches a pitch of the single-lead thread of the third portion 96. In another embodiment, a higher pitch of the thread in the third threaded portion 96 can be used to facilitate compression of the femoral head onto the shaft 82.

An exemplary method of use of the bone fixation system 800 is substantially similar to the method of use of the system 100 described in detail earlier with respect to FIGS. 11-20. Specifically, once the fractured bone 1 has been provisionally brought into a corrected alignment and an incision has been made, one or more guide wire are inserted into a center of the femoral head at a desired angle until a distal end of the guide wire extends into the subchondral bone, as those skilled in the art will understand. A known reaming device (not shown) is then guided over the guide wire to ream a bore hole for the insertion of an implant according to the invention. The implant shaft 830 is then inserted through the channel 818 of the second portion 806 of the bone plate 802 until engagement of the abutment 822 with the proximal end 839 of the cutout 838 prevents further distal movement of the implant shaft 830. The assembled bone plate 802 and implant shaft 830 are then attached to the insertion instrument 40 including an arm portion 42 and an elongated shaft portion 44, a distal end 46 of which removably grasps the recesses 805 of the bone plate 802. Once the bone plate 802 has been attached to the insertion instrument 40, an impactor may be inserted through the bone plate 802 and implant shaft 830 to impact the system 800 into the bone. The impactor (not shown) and the guide wire (not shown) may then be removed from the bone, leaving the insertion instrument 40 and system 800 positioned in the bone.

Figure 49:
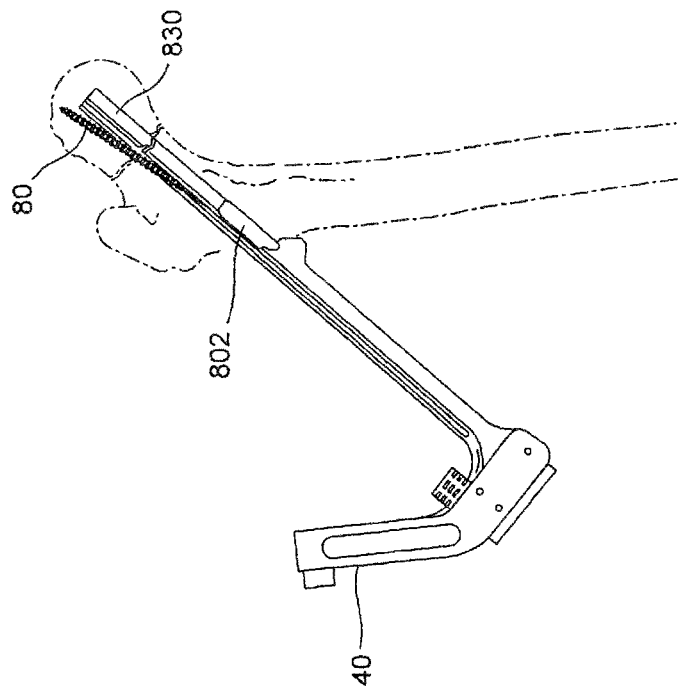
FIG. 49 shows a fourth surgical step for use of the bone fastener assembly of FIG. 36.
Figure 48:
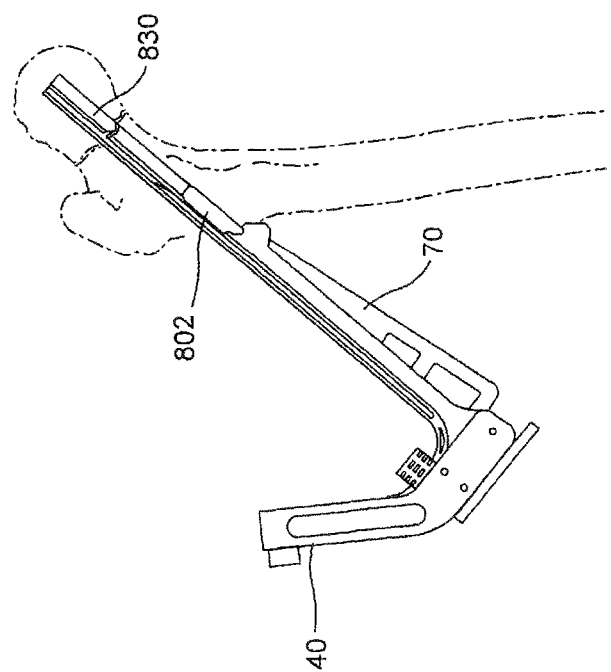
FIG. 48 shows a third surgical step for use of the bone fastener assembly of FIG. 36.

As shown in FIGS. 48-49, the second protection sleeve 70 is then inserted through the second opening 50 and through the elongated shaft 44 until a distal end thereof is seated against the implant shaft 830. A drilling mechanism (not shown) may be inserted through the second channels 78 and 844 to prepare the bone 1 for the anti-rotation bone screw 80. As those skilled in the art will understand, in softer bone, pre-drilling may not be necessary. As would be understood by those skilled in the art, a driving mechanism (not shown) may then be used to insert the anti-rotation screw 80 through the second protection sleeve 70 and implant shaft 830 and into the bone 1. The second protection sleeve 70 and insertion instrument 40 may then be removed from the body, leaving the system 800 implanted in the bone 1. Once implanted, the head of the femur is prevented from rotation relative to the bone 1 via the anti-rotation screw 80 and bone plate 802.

As shown in FIG. 50, the first protection sleeve 60 is then inserted through the first opening 48 in the insertion instrument 40 to guide the drilling of a hole into the bone 1 to permit insertion of the bone fixation element 10 (i.e., a bicortical shaft screw) therein. Specifically, a drilling mechanism known in the art may be inserted through the first protection sleeve 60 to drill an opening through the locking hole 808 of the bone plate 802 and into the bone 1. The drilling mechanism may then be removed and the bone fixation element 10 may be inserted through the first protection sleeve 60 and bone plate 802 and into the bone 1.

Figure 51:
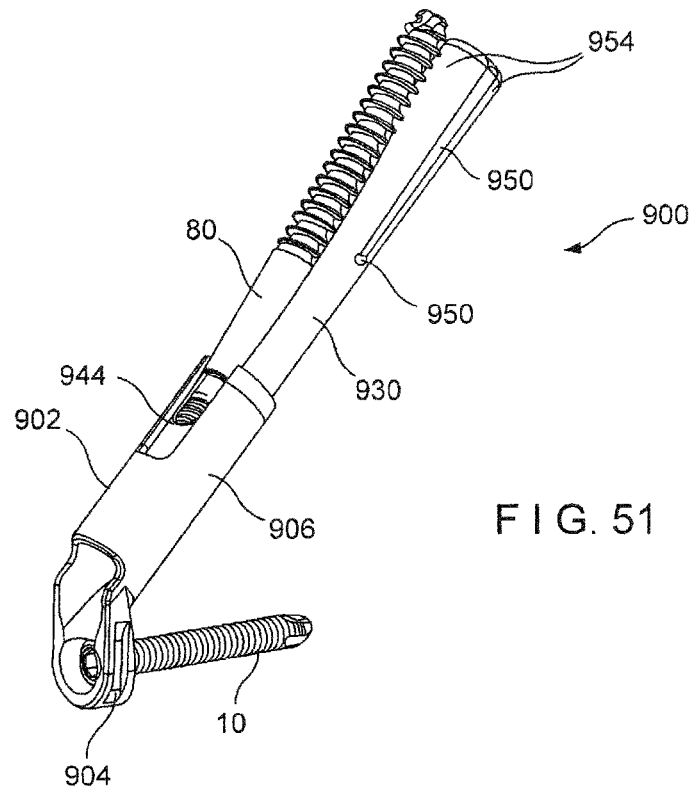
FIG. 51 shows a perspective view of a bone fastener assembly according to another embodiment of the invention.
Figure 52:
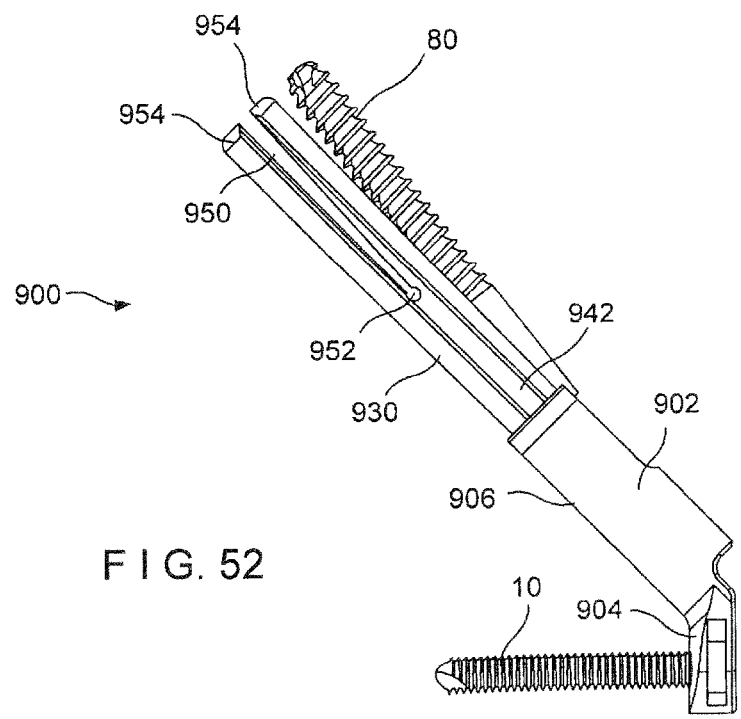
FIG. 52 shows a side view of the bone fastener assembly of FIG. 51.

FIGS. 51-52 depict a system 900 according to yet another embodiment of the invention. The system 900 is formed substantially similarly to the system 800 and includes a bone plate 902 having first and second portions 904, 906 and an implant shaft 930 with one or more elastic deflecting structures at a distal end thereof. The implant shaft 930 includes an elongated channel 942 extending therethrough from a proximal end (not shown) to a distal end. A second channel 944 extends therethrough at an angle relative to a central longitudinal axis thereof to house the anti-rotation screw 80, as described in greater detail with respect to earlier embodiments. The implant shaft 930 further comprises a plurality of elongated slots 950 extending proximally from the distal end 934 and terminating at a substantially circular cutout at proximal ends 952. In an exemplary embodiment, the implant shaft 930 may include two slots 950 provided on opposing walls of the implant shaft 930 to define two compliant arms 954. It is noted however, that any number of slots 950 may be provided without deviating from the scope of the invention. As those skilled in the art will understand, the compliant arms 954 increase an overall elasticity of the implant shaft 930 by distributing a peak load applied to the distal end 934, permitting the shaft 930 to deform instead of fracturing when subjected to excessive loads. By allowing for deformation of the implant shaft 930, the compliant arms 954 prevent inadvertent penetration of the implant shaft 930 through the bone, as those skilled in the art will understand.

Figure 53:
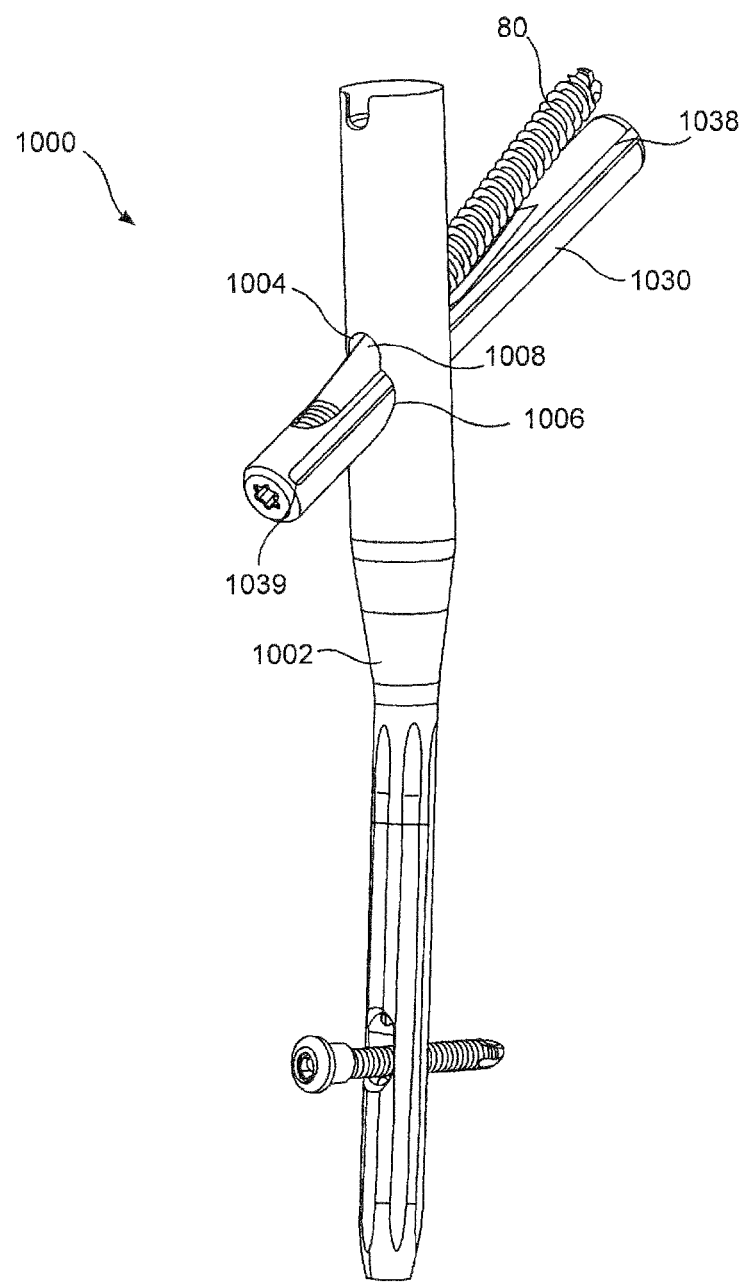
FIG. 53 shows a perspective view of a bone fastener assembly according to another embodiment of the invention.

FIG. 53 depicts a system 1000 according to another embodiment of the invention. The system 1000 depicts an implant shaft 1030 formed substantially similar to the implant shafts 130, 830 described above. However, instead of being inserted through a bone plate, the implant shaft 1030 is insertable through an intramedullary nail 1002. The intramedullary nail 1002 includes a transverse opening 1004 extending therethrough, the transverse opening 1004 having a shape formed by first and second overlapping circular channels 1006, 1008. The first circular channel 1006 is configured to permit insertion of the implant shaft 1030 therethrough and extends through the intramedullary nail 1002 at a first angle. The second circular channel 1008 is open to the first circular channel and extends through the intramedullary nail 1002 at a second angle different than the first angle. Specifically, an angle of the second circular channel 1008 substantially matches an angle of the second channel 144 relative to the first channel 142 of the implant shaft 1030. Thus, the anti-rotation screw 80 inserted through the second channel 144 is guided through the second channel 1008 and out of an opposing wall of the intramedullary nail 1002.

An outer wall of the implant shaft 1030 may include a cutout 1038 configured to engage a respectively shaped abutment (not shown) provided in the first channel 1006. Engagement of the abutment (not shown) with the cutout 1038 prevents rotation of the implant shaft 1030 relative to the transverse opening 1004. Furthermore, engagement of the abutment (not shown) with a proximal end 1039 of the cutout 1038 limits a depth of insertion of the implant shaft 1030 into the bone, as described in greater detail in earlier embodiments.

Figure 54:
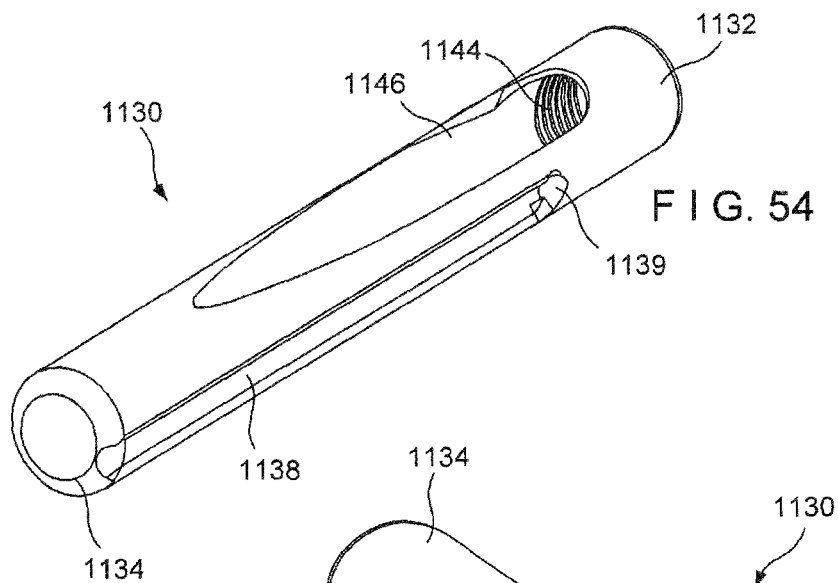
FIG. 54 shows a first perspective view of an implant shaft according to another embodiment of the invention.
Figure 55:
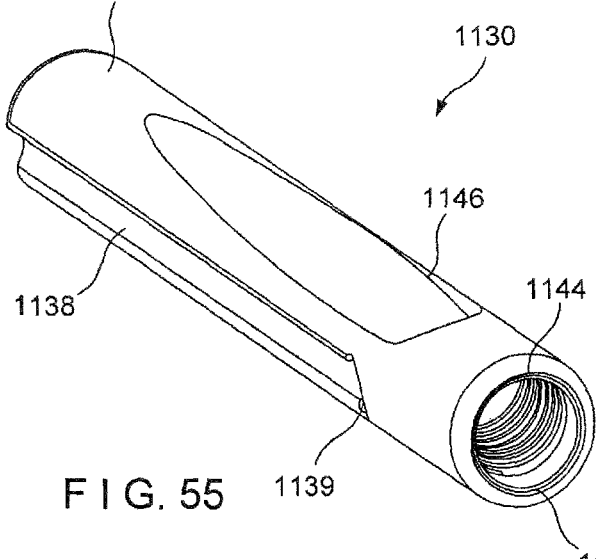
FIG. 55 shows a second perspective view of the implant shaft of FIG. 54.
Figure 56:
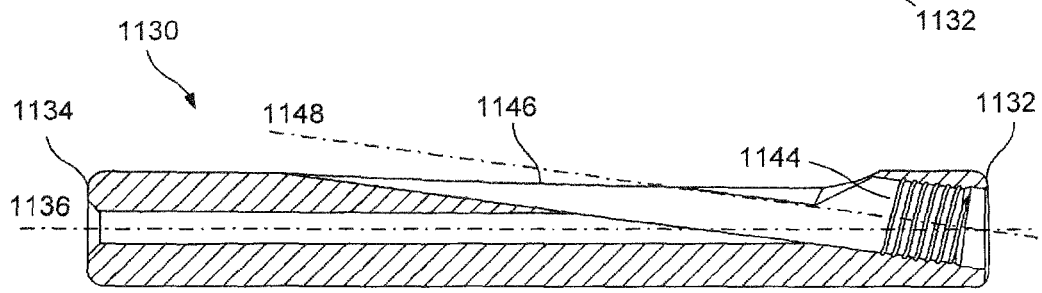
FIG. 56 shows a cross-sectional view of the implant shaft of FIG. 54.

FIGS. 54-56 depict an implant shaft 1130 according to yet another embodiment according to the invention. The implant shaft 1130 is formed substantially similarly to the implant shafts 130, 830 except as noted hereinafter. The implant shaft 1130 may be used with any of the bone plates 102, 602, 802, 902 and intramedullary nails 1002 disclosed above. The implant shaft 1130 is formed as an elongated substantially cylindrical member extending from a proximal end 1132 to a substantially blunt distal end 1134 along a central longitudinal axis 1136. An outer surface of the implant shaft 1130 comprises an elongated cutout 1138 extending from a proximal end 1139 to the distal end 1134, the cutout 1138 being formed substantially similar to the cutout 838. However, unlike earlier embodiments, the implant shaft 1130 does not comprise a central longitudinal channel extending therethrough. Rather, the implant shaft 1130 comprises only a channel 1144 extending therethrough along an axis 1148 from the proximal end 1132 to a distal opening 1146 on a side wall of the implant shaft 1130 to receive, for example, an anti-rotation screw (not shown) therethrough. Accordingly, unlike earlier embodiments, which may optionally be guided over a pre-positioned guide wire into the bone, the exemplary implant shaft 1130 may be inserted into the bone after removal of the guide wire therefrom. That is, the implant shaft 1130 may be guided into the bone via a hole pre-drilled therein.

Although the invention and its advantages have been described in detail, it should be understood that various changes, substitutions, and alterations can be made herein without departing from the spirit and scope of the invention as defined by the appended claims. For example, any of the implant shafts and bone plates disclosed herein may optionally be coated with Diamond-Like Carbon (DLC) to prevent osseointegration thereof, as those skilled in the art will understand and/or to reduce friction and therefore improve telescoping between the bone plate and the implant shaft. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

FIGS. 57-62 depict a kit 1200 according to another embodiment of the invention as required for the completion of a bone fixation procedure. The kit 1200 is formed substantially similarly to the kit 750 described earlier, with like elements being referenced with like reference numerals. However, whereas the kit 750 is configured for single-use, the kit 1200 may be used any number of times to perform multiple procedure. It is noted that the kit 1200 may also be configured for single-use without deviating from the scope of the invention. Furthermore, whereas the removable shaft portion 44 of the kit 750 engages the instrument 40 with a click/snap-fit engagement, a removable shaft portion 1250 of the kit 1200 engages an instrument 1240 with a threaded engagement, as will be described in greater detail hereinafter. It is noted, however, that the kit 1200 may also employ the snap-fit engagement of kit 750 without deviating from the scope of the invention. The kit 1200 according to the invention includes an insertion instrument 1240 extending from a proximal end 1242 including a curved arm 1244 to a distal end 1246. A first opening 1247 extends through the arm 1244 to guide the first protection sleeve 60 therethrough, as will be described in greater detail with respect to the exemplary method below. A second opening 1248 extends into the proximal end 1242 permitting insertion of the removable shaft portion 1250 thereinto. The instrument 1240 also comprises an elongated slot 1249 on a side wall thereof to accommodate the width of the shaft portion 1250 when inserted therein.

The removable shaft portion 1250 includes a first elongated shaft portion 1252 extending from a first proximal end 1254 to a distal end 1256 and including a first channel 1258 extending therethrough. In an operative configuration, a longitudinal axis 1260 of the first channel 1258 is substantially aligned with the longitudinal axis 136 of the implant shaft 130. The removable shaft portion 1250 further comprises a second elongated shaft portion 1262 formed substantially similarly to the second protection sleeve 70 and extending from a second proximal end 1264 to the distal end 1256. A second channel 1268 extends through the second shaft portion 1262 along a longitudinal axis 1270 offset from the longitudinal axis 1260 by approximately 7.5° to align with the axis 148 of the implant shaft 130, as described in greater detail with respect to earlier embodiments. The first and second elongated shaft portions 1252, 1262 extend to a common distal end 1256 via a connecting element 1280. The connecting element 1280 according to this embodiment comprises an elongated slot 1282 extending through a side wall thereof to permit insertion of the anti-rotation screw 20 therethrough and through the implant 130 to extend into the bone, as will be described in greater detail with respect to the exemplary method below.

The first elongated shaft portion 1252 includes a locking element 1284 at the first proximal end 1254. The locking element 1284 includes a threaded portion 1286 and a screw 1288 which may be rotated (e.g., manually by a user) to screw the threaded portion 1286 into a corresponding threaded region (not shown) provided within the opening 1248 of the instrument 1240. Specifically, rotation of the screw 1288 rotates the entire first elongated shaft portion 1252 relative to the connecting element 1280. In one embodiment of the invention, the first elongated shaft portion 1252 is removably attached to the connecting element 1280. In another embodiment, the first elongated shaft portion 1252 is permanently attached to the connecting element 1280 and axially movable relative thereto within a predetermined range of motion corresponding to an axial length of the threaded portion 1286 to permit screwing and unscrewing thereof into the instrument 1240, as those skilled in the art will understand. The second elongated shaft portion 1262 may also be either permanently or removably attached to the connecting element 1280 as those skilled in the art will understand.

Figure 58:
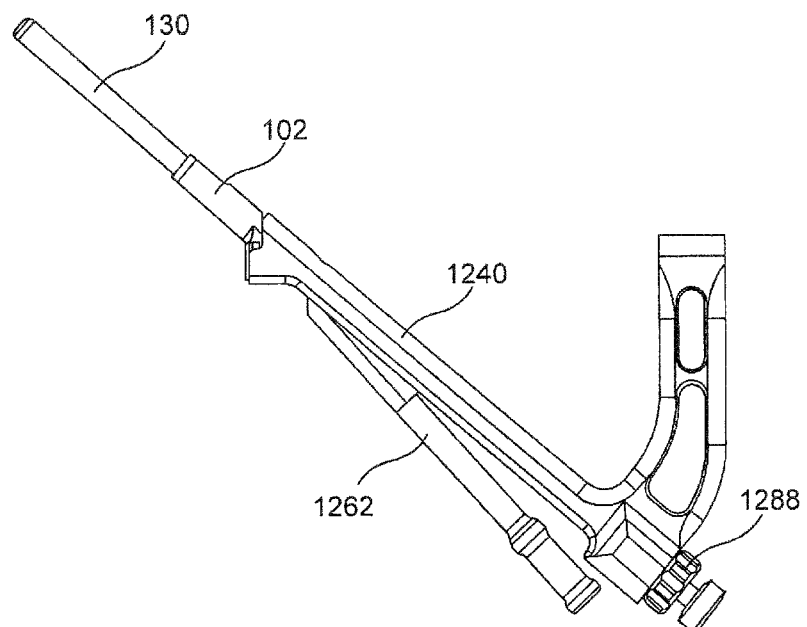
FIG. 58 shows a perspective view of the device of FIG. 57 in a second operative configuration.

In accordance with an exemplary method according to the invention, a patient is placed in a supine position on an operating table and a fractured femur is provisionally brought into a corrected alignment via one or more of traction, abduction and internal rotation as would be understood by those skilled in the art. An incision is formed in the skin and the bone is reamed to create a bore hole for the insertion of an implant according to the invention. The assembled bone plate 102 and implant shaft 130 are then attached to the insertion instrument 1240 via a sliding engagement between the distal end 1246 and a proximal end of the bone plate 102, as described in greater detail in earlier embodiments. The removable shaft portion 1250 is then inserted into the opening 1248 such that the distal end 1256 extends adjacent to the distal end 1246 of the instrument 1240, as shown in FIG. 58. The screw 1288 is then rotated to threadedly drive the first elongated shaft portion 1252 into the instrument 1240 and into threaded engagement with a threaded portion (not shown) of the opening 1248. The locking element 1284 is configured so that, when the screw 1288 comes into contact with an outer surface of the instrument 1240, the first elongated shaft portion 1252 is locked against rotation or axial movement relative to the instrument 1240.

Figure 59:
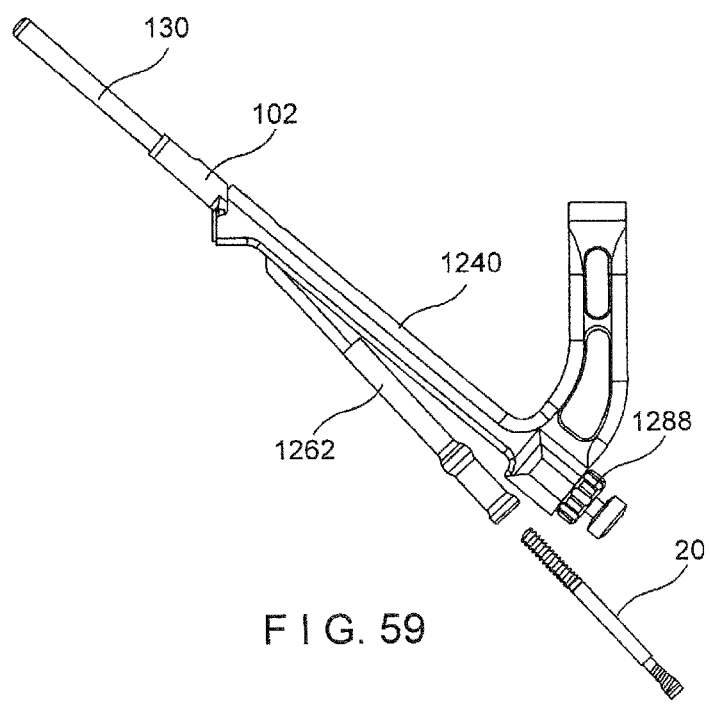
FIG. 59 shows a perspective view of the device of FIG. 57 in a third operative configuration.
Figure 60:
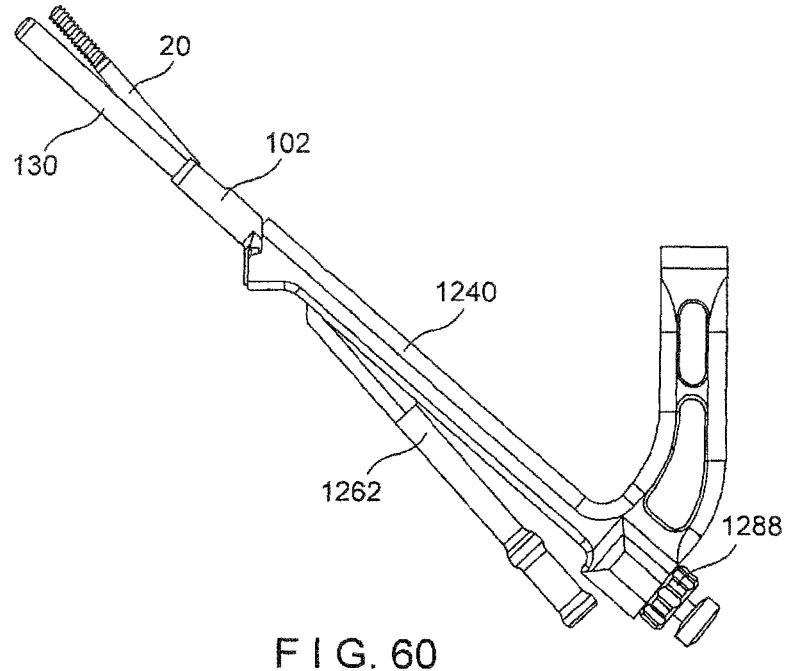
FIG. 60 shows a perspective view of the device of FIG. 57 in a fourth operative configuration.
Figure 61:
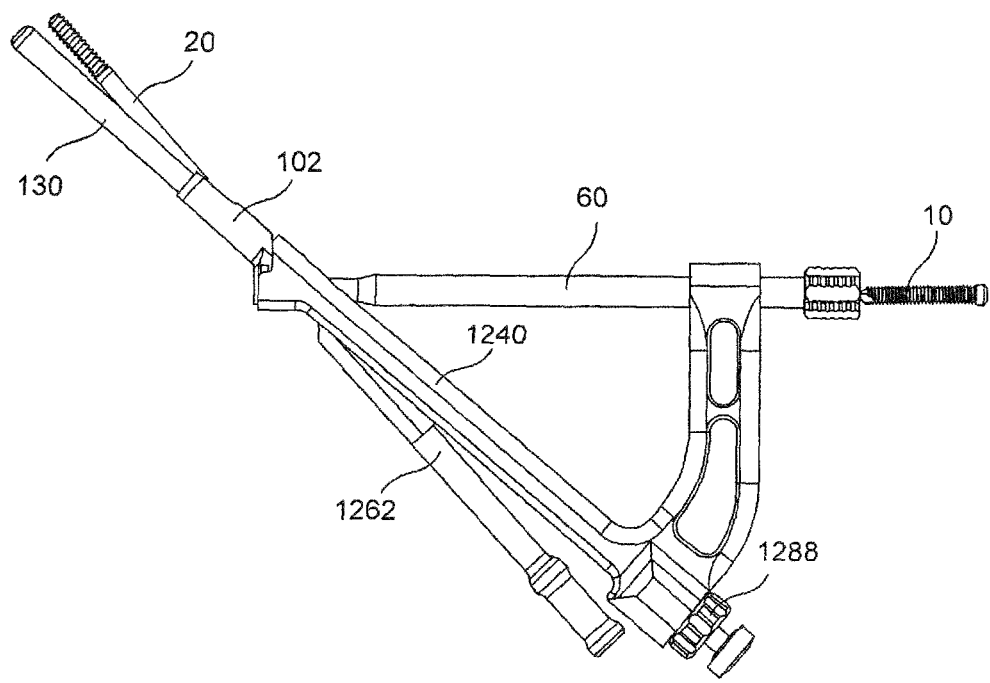
FIG. 61 shows a perspective view of the device of FIG. 57 in a fifth operative configuration.
Figure 62:
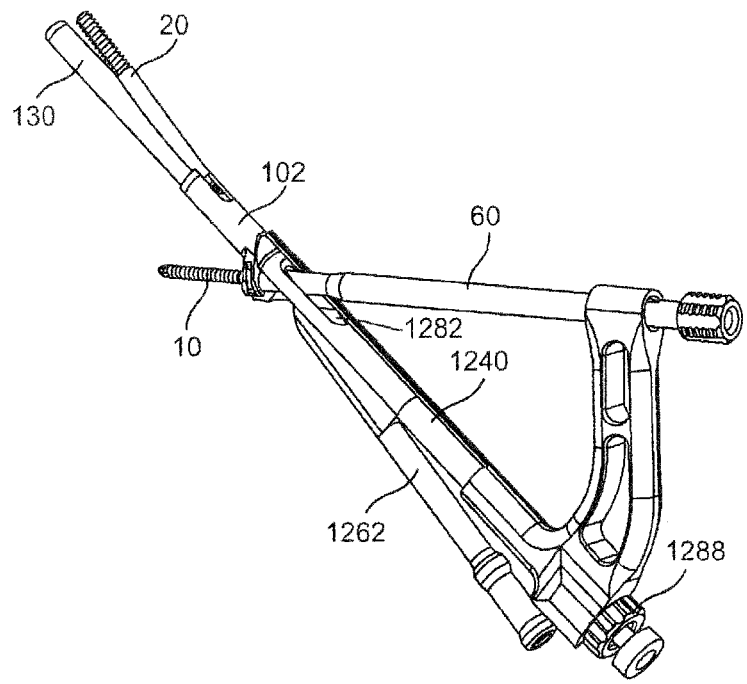
FIG. 62 shows a first perspective view of the device of FIG. 57 in a sixth operative configuration.
Figure 63:
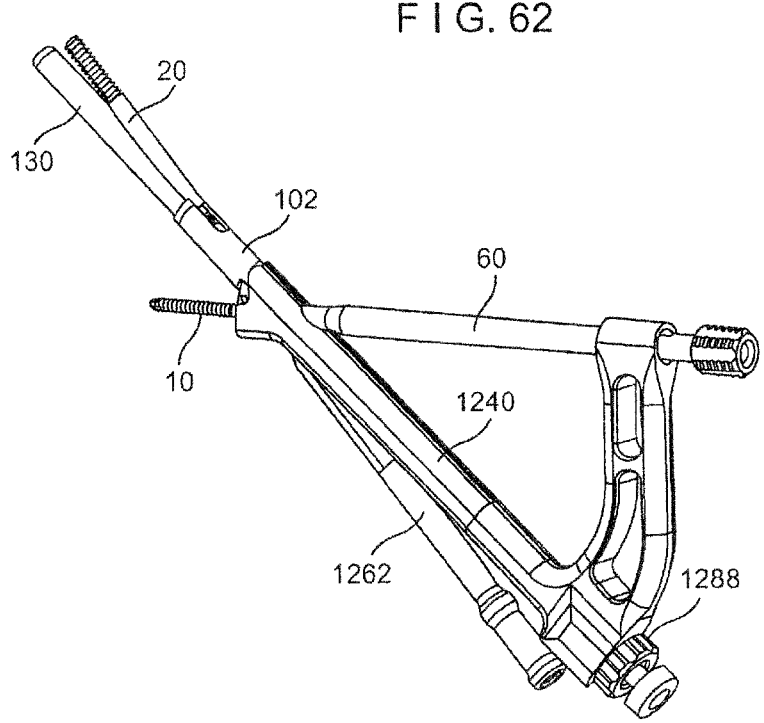
FIG. 63 shows a second perspective view of the device of FIG. 57 in the sixth operative configuration.

Once the shaft portion 1250 has been locked to the instrument 1240, and the bone fixation system 100 inserted into the bone, a drilling mechanism (not shown) may be inserted through the channel 1270 to prepare the bone for the anti-rotation bone screw 20. As those skilled in the art will understand, in softer bone, pre-drilling may not be necessary. A driving mechanism (not shown) may then be used to insert the anti-rotation screw 20 through the second elongated shaft portion 1262 and implant shaft 130 and into the bone, as shown in FIGS. 59 and 60. In the implanted configuration, a distal end of the anti-rotation screw 20 is separated from a distal end of the implant shaft 130 by approximately 5 mm. As shown in FIGS. 61-63, the first protection sleeve 60 is then inserted through the first opening 1247 in the insertion instrument 1240. As described in greater detail in earlier embodiments, the first protection sleeve 60 extends through the first opening 1247 and into the distal end 46 of the insertion instrument 40 at a predetermined angle relative to the angle of the first elongated shaft portion 1252 (e.g., 45°, etc.) until a distal end thereof is in contact with the locking hole 108, as shown in the partial cutaway view of FIG. 62. An optional drilling mechanism known in the art may be inserted through the first protection sleeve 60 to drill an opening through the locking hole 108 of the bone plate 102 and into the bone. The drilling mechanism may then be removed and the bone fixation element 10 may be inserted through the first protection sleeve 60 and bone plate 102 and into the bone 1. The first protection sleeve 60 and instrument 1240 may then be removed, leaving the system 100 implanted in the bone. It is noted that although the exemplary method depicts the insertion of the anti-rotation screw 20 followed by the bicortical screw 10 first, the order of insertion may be changed without deviating from the scope of the invention to suit, for example, a surgeon's preference. Furthermore, although the kit 1200 is described with respect to the system 100, the kit 1200 may be employed with any of the systems 200, 300, 400, 500, 600, 800 disclosed herein.

It will be appreciated by those skilled in the art that various modifications and alterations of the invention can be made without departing from the broad scope of the appended claims. Some of these have been discussed above and others will be apparent to those skilled in the art.

What is claimed is:

1. A method for implanting a bone fixation assembly into a bone, comprising:
   inserting an implant shaft through a second opening extending through a bone plate, the bone plate having a first plate portion and a second plate portion, the first plate portion having a first opening extending therethrough along a first opening axis and the second plate portion having the second opening extending therethrough along a second opening axis, the implant shaft extending from a proximal end to a distal end along a central longitudinal axis and including a first channel extending from the proximal end to a side opening formed in a side wall thereof along a first channel axis;
   inserting the implant shaft into a head of the bone until the first portion of the bone plate is positioned over an outer surface of the bone and a portion of the second portion is received within the bone; and
   inserting an anti-rotation screw through the first channel until a head of the screw lockingly engages the proximal end of the first channel and a distal end of a shaft of the screw extends out of the side opening into the bone to prevent rotation of a head of the bone relative to the implant shaft, the anti-rotation screw extending along the first channel axis to penetrate the bone angled relative to the second opening axis.

2. The method of claim 1, wherein the implanted anti-rotation screw is offset from the central longitudinal axis by approximately 7.5°.

3. The method of claim 1, wherein the implanted anti-rotation screw is offset from the central axis by an angle greater than 5°.

4. The method of claim 1, further comprising the step of aligning a first surface provided on the outer wall of the implant shaft with a corresponding second surface on an outer wall of the second opening to prevent rotation of the implant shaft relative to the bone plate.

5. The method of claim 4, wherein the first and second surfaces are shaped to mechanically interlock to prevent rotation of the implant shaft relative to the second opening while permitting longitudinal movement of the shaft relative to the second opening.

6. The method of claim 4, wherein the first surface is one of flat and hemispherical.

7. The method of claim 4, wherein the implant shaft is inserted through the second opening of the bone plate until a protrusion at a proximal end of the first surface engages a proximal end of the second surface.

8. The method of claim 1, further comprising the step of inserting a first locking screw through the first opening and into the bone.

9. The method of claim 1, further comprising the step of inserting a second locking screw through a third opening extending through a third portion of the bone plate and into the bone.

10. The method of claim 1, further comprising the step of inserting a guide wire into the bone at a desired angle to guide the insertion of the implant shaft into the bone.

11. The method of claim 10, wherein the implant shaft includes a second channel extending from the proximal end to the distal end along a second channel axis, the second channel receiving the guide wire therethrough to aid in insertion.

12. The method of claim 1, wherein the implant shaft is inserted into the bone via an insertion instrument coupleable to the bone plate.

13. The method of claim 1, wherein the implant shaft is impacted into the bone.

14. The method of claim 1, further comprising the step of drilling a hole into the bone along the first channel axis.

15. A method for assembling a bone fixation assembly, comprising:
   inserting an implant shaft through a second opening extending through a bone plate, the implant shaft engaging the second opening with a form fit, the bone plate having a first plate portion and a second plate portion, the first plate portion having a first opening extending therethrough along a first opening axis and the second plate portion having the second opening extending therethrough along a second opening axis, the implant shaft extending from a proximal end to a distal end along a central longitudinal axis and including a first channel extending from the proximal end to a side opening formed in a side wall thereof along a first channel axis, the second opening being configured to receive the implant shaft therethrough to permit insertion thereof into a head of a bone along the second opening axis so that a bone fixation element inserted through the first channel extends through the implant shaft along the first channel axis to penetrate the bone angled relative to the second opening axis.

16. The method of claim 15, further comprising the step of aligning a first surface provided on the outer wall of the implant shaft with a corresponding second surface on an outer wall of the second opening to prevent rotation of the implant shaft relative to the bone plate.

17. The method of claim 16, wherein the first and second surfaces are shaped to mechanically interlock to prevent rotation of the implant shaft relative to the second opening while permitting longitudinal movement of the implant shaft relative to the second opening.

18. The method of claim 16, wherein the first surface is one of flat and hemispherical.

19. The method of claim 15, wherein the implant shaft is inserted through the second opening of the bone plate until a protrusion at a proximal end of the first surface engages a proximal end of the second surface.

* * * * *